US009713604B2

(12) United States Patent
Dreher

(10) Patent No.: US 9,713,604 B2
(45) Date of Patent: Jul. 25, 2017

(54) ANTIOXIDANT COMPOSITIONS AND METHODS OF USING THE SAME

(71) Applicant: Anteis SA, Plan-les-Ouates (CH)

(72) Inventor: Frank Dreher, San Francisco, CA (US)

(73) Assignee: ANTEIS SA, Plan-les-Ouates (CH)

(*) Notice: Subject to any disclaimer, the term of this patent is extended or adjusted under 35 U.S.C. 154(b) by 486 days.

(21) Appl. No.: 14/258,074

(22) Filed: Apr. 22, 2014

(65) Prior Publication Data
US 2014/0315995 A1   Oct. 23, 2014

Related U.S. Application Data

(60) Provisional application No. 61/875,294, filed on Sep. 9, 2013, provisional application No. 61/830,423, filed on Jun. 3, 2013, provisional application No. 61/814,791, filed on Apr. 22, 2013.

(51) Int. Cl.
| A61K 31/35 | (2006.01) |
| A61K 31/355 | (2006.01) |
| A61K 31/34 | (2006.01) |
| A61K 31/195 | (2006.01) |
| A61K 31/375 | (2006.01) |
| A61K 31/197 | (2006.01) |
| A61K 31/353 | (2006.01) |
| A61K 8/67 | (2006.01) |
| A61K 8/44 | (2006.01) |
| A61Q 19/08 | (2006.01) |
| A61K 8/58 | (2006.01) |
| A61Q 19/00 | (2006.01) |
| A61K 8/891 | (2006.01) |
| A61K 31/198 | (2006.01) |
| A61K 31/695 | (2006.01) |
| A61K 9/00 | (2006.01) |
| A61K 47/34 | (2017.01) |

(52) U.S. Cl.
CPC .............. *A61K 31/375* (2013.01); *A61K 8/44* (2013.01); *A61K 8/585* (2013.01); *A61K 8/676* (2013.01); *A61K 8/678* (2013.01); *A61K 8/891* (2013.01); *A61K 9/0014* (2013.01); *A61K 31/197* (2013.01); *A61K 31/198* (2013.01); *A61K 31/353* (2013.01); *A61K 31/355* (2013.01); *A61K 31/695* (2013.01); *A61K 47/34* (2013.01); *A61Q 19/00* (2013.01); *A61Q 19/004* (2013.01); *A61Q 19/08* (2013.01); *A61K 2800/31* (2013.01); *A61K 2800/522* (2013.01)

(58) Field of Classification Search
CPC .... A61K 31/35; A61K 31/355; A61K 31/375; A61K 31/195
USPC ................. 514/456, 458, 474, 565
See application file for complete search history.

(56) References Cited

U.S. PATENT DOCUMENTS

| 6,194,452 B1 | 2/2001 | Murad |
| RE38,623 E | 10/2004 | Hernandez et al. |
| 6,805,880 B1 | 10/2004 | Hojgaard et al. |
| 9,044,409 B2 | 6/2015 | Carola et al. |
| 2003/0027772 A1 | 2/2003 | Breton |
| 2003/0031797 A1 | 2/2003 | Delmotte et al. |
| 2003/0118536 A1 | 6/2003 | Rosenbloom |
| 2005/0158396 A1 | 7/2005 | Kraechter et al. |
| 2005/0286158 A1 | 12/2005 | Bui et al. |
| 2011/0158922 A1* | 6/2011 | Dupont ............... A61K 8/73 424/59 |
| 2013/0216596 A1* | 8/2013 | Viladot Petit ......... A61K 8/11 424/401 |

FOREIGN PATENT DOCUMENTS

| CN | 1 943 572 A | 4/2007 |
| EP | 1 430 882 A2 | 6/2004 |
| EP | 1 430 882 A3 | 6/2004 |
| EP | 1 430 882 B1 | 6/2004 |
| EP | 1 508 327 A1 | 2/2005 |
| EP | 1 508 327 B1 | 2/2005 |
| FR | 2 825 277 A1 | 12/2002 |
| FR | 2 825 277 B1 | 12/2002 |
| FR | 2 946 253 A1 | 12/2010 |
| FR | 2 946 253 B1 | 12/2010 |
| GB | 2 259 014 A | 3/1993 |
| GB | 2 259 014 B | 3/1993 |
| WO | WO-00/02535 A1 | 1/2000 |
| WO | WO-2014/188276 A2 | 11/2014 |
| WO | WO-2014/188276 A3 | 11/2014 |

OTHER PUBLICATIONS

Afaq, F. et al. (Sep.-Oct. 2002). "Photochemoprevention by botanical antioxidants," *Skin Pharmacol Appl Skin Physiol* 15(5):297-306.
Afaq, F. et al. (Jun. 2009, e-published Mar. 6, 2009). "Protective effect of pomegranate-derived products on UVB-mediated damage in human reconstituted skin," *Exp Dermatol* 18(6):553-561.
Ameri, M. et al. (Feb. 2010, e-published Dec. 15, 2009). "Parathyroid hormone PTH(1-34) formulation that enables uniform coating on a novel transdermal microprojection delivery system," *Pharm Res* 27(20):303-313.
Akron, S.T. et al. (Sep. 2007). "Persistent delayed-type hypersensitivity reaction to injectable non-animal-stabilized hyaluronic acid," *J Cosmet Dermatol* 6(3):167-171.
Baschong, W. et al. (May-Jun. 2001). "Direct evidence for bioconversion of vitamin E acetate into vitamin E: an ex vivo study in viable human skin," *J Cosmet Sci* 52(3):155-161.
Baumann, L. et al. (Jun. 2009). "Natural ingredients in cosmetic dermatology," *J Drugs Dermatol* 8(6Suppl):s5-9.

(Continued)

*Primary Examiner* — Raymond Henley, III
(74) *Attorney, Agent, or Firm* — Mintz Levin Cohn Ferris Glovsky and Popeo, P.C.

(57) ABSTRACT

The invention provides non-irritating, stable topical compositions including at least Vitamin C, Vitamin E and a polyphenol antioxidant. Such compositions can be used to facilitate the prevention or treatment of free oxygen, nitrogen, and/or other free radical related skin damage. Also provided are methods for modifying free radical damage to skin by administering such compositions in an amount sufficient to treat and/or prevent free radical damage to the skin.

37 Claims, 7 Drawing Sheets

(56) References Cited

OTHER PUBLICATIONS

Beitner, H. (Oct. 2003). "Randomized, placebo-controlled, double blind study on the clinical efficacy of a cream containing 5% α-lipoic acid related to photoageing of facial skin," *Br J Dermatol* 149(4):841-849.

Berneburg, M. et al. (Aug. 2005). "Creatine supplementation normalizes mutagenesis of mitochondrial DNA as well as functional consequences," *Journal of Investigative Dermatology* 125(2):213-220.

Berson, D.S. (Jul. 2008). "Natural Antioxidants," *J Drugs Dermatol* 7(7 Suppl):s7-12.

Bialy, T.L. et al. (Dec. 2002). "Dietary factors in the prevention and treatment of nonmelanoma skin cancer and melanoma," *Dermatol Surg* 28(12):1143-1152.

Boehm, K. et al. (Jul. 2009). "Green tea (*Camellia sinensis*) for the prevention of cancer," *Cochrane Database Systematic Reviews* 8(3):CD005004, 63 pages.

Boelsma, E. et al. (May 2001). "Nutritional skin care: health effects of micronutrients and fatty acids," *Am J Clin Nutr* 73(5):853-864.

Camouse, M.M. et al. (Jun. 2009). "Topical application of green and white tea extracts provides protection from solar-simulated ultraviolet light in human skin," *Exp Dermatol* 18(6):522-526.

Chang, H. et al. (Jun. 2003). "The role of $H_2O^2$ as a mediator of UVB-induced apoptosis in keratinocytes," *Free Radic Res* 37(6):655-663.

Chen, L.L. et al. (Oct. 2012). "From the bottle to the skin: challenges in evaluating antioxidants," Photodermkatol Phtoimmunol Phtomed 28(5);228-234.

Chiu et al. (Jul. 2005). "Double-blinded, placebo-controlled trial of green tea extracts in the clinical and histologic appearance of photoaging skin," *Dermatol Surg* 31(7 Pt 2):855-860.

Connor, M.J. et al. (Aug. 1987). "Depletion of cutaneous glutathione by ultraviolet radiation," *Photochem Photbiol* 46(2):239-245.

Dai, F. et al. (Oct. 2008, e-published May 23, 2008). "Antioxidant synergism of green tea polyphenols with alpha-tocopherol and L-ascorbic acid in SDS micelles" *Biochimie* 90(10):1499-1505.

Darr, D. et al. (Sep. 1992). "Topical vitamin C protects porcine skin from ultraviolet radiation-induced damage," *Br J Dermatol* 127(3):247-353.

Darr, D. et al. (Jul. 1996). "Effectiveness of antioxidants (vitamin C and E) with and without sunscreens as topical photoprotectants," *Acta Derm Venereol* 76(4):264-268.

Davidson, J.M. et al. (Jan. 3, 1997). "Ascorbate differentially regulates elastin and collagen biosynthesis in vascular smooth muscle cells and skin fibroblasts by pretranslational mechanisms," *J Biol Chem* 272(1):345-352.

Ditre, C. et al. (Dec. 2008). "Innovations in natural antioxidants and their role in dermatology," *Cutis* 82(6 Suppl):2-16.

Dreher, F. et al. (Aug. 1998). "Topical melatonin in combination with vitamins E and C protects skin from ultraviolet-induced erythema: a human study in vivo," *Br J Dermatol* 139(2):332-339.

Dreher, F. et al. (2010). "Antioxidants", Chapter 13 in *Textbook of Cosmetic Dermatology*, $4^{th}$ edition, pp. 115-122.

Edwards, A.M. et al. (Aug. 1994). "Visible light effects on tumoral cells in a culture medium enriched with tryptophan and riboflavin," *J Photochem Photobiol B* 24(3):179-186.

Elmets, C.A. et al. (Mar. 2001). "Cutaneous photoprotection from ultraviolet injury by green tea polyphenols," *J Am Acad Dermatol* 44(3):425-432.

Farris, P.K. (Jul. 2005). "Topical vitamin C: a useful agent for treating photoaging and other dermatologic conditions," *Dermatol Surg* 31(7 Pt 2):814-817.

Farris, P. (Sep.-Oct. 2007). "Idebenone, green tea, and Coffeeberry extract: new and innovative antioxidants," *Dermatol Ther* 20(5):322-329.

Frei, B. et al. (Oct. 2003). "Antioxidant activity of tea polyphenols in vivo: evidence from animal studies," *J Nutr* 133(10):3275S-3284S.

Fuchs, J. (Nov. 1998). "Potentials and limitations of the natural antioxidants RRR-alpha-tocopherol, L-ascorbic acid and beta-carotene in cutaneous photoprotection," *Free Radic Biol Med* 25(7):848-873.

Gallarate. M. et al. (Oct. 25, 1999). "On the stability of ascorbic acid in emulsified systems for topical and cosmetic use," *Int J Pharm* 188(2):233-241.

Gonzalez, S. et al. (Feb.-Apr. 1997). "Topical or oral administration with an extract of Polypodium leucotomos prevents acute sunburn and psoralen-induced phototoxic reactions as well as depletion of Langerhans cells in human skin," *Photodermatol Photoimmunol Photomed* 13(1-2):50-60.

Kang, S. et al. (May 2003). "Topical N-acetyl cysteine and genistein prevent ultraviolet-light-induced signaling that leads to photoaging in human skin in vivo," *J Invest Dermatol* 120(5):835-841.

Katiyar, S.K. et al. (Feb. 2001). "Green tea polyphenol (−)-epigallocatechin-3-gallate treatment of human skin inhibits ultraviolet radiation-induced oxidative stress," *Carcinogenesis* 22(2):287-294.

Kramer, K.A. et al. (Feb. 1997). "UVB induced photooxidation of vitamin E," *Chem Res Toxicol* 10(2):219-224.

Kramer-Stickland, K. et al. (Aug. 1998). "Effect of UVB on hydrolysis of alpha-tocopherol acetate to alpha-tocopherol in mouse skin," *J Invest Deramtol* 111(2);302-307.

Krutmann, J. et al. (Aug. 2009). "Role of Mitochondria in Photoaging of Human Skin: The Defective Powerhouse Model," *J. Investigative Dermatology Symposium Proceedings* 14(1):44-49.

Hadshiew, I. et al. (1997). "Effects of topically applied antioxidants in experimentally provoked polymorphous light eruption," *Dermatology* 195(4):362-368.

Herrling, T. et al. (Aug. 2012, e-published May 5, 2012). "The Radical Status Factor (RSF): a novel metric to characterize skin products," *Int J Cosm Sci* 34(4):285-290.

Hsu, S. (Jun. 2005). "Green tea and the skin," *J Am Acad Dermatol* 52(6):1049-1059.

Humbert, P.G. et al. (Jun. 2003). "Topical ascorbic acid on photoaged skin. Clinical, topographical and ultrastructural evaluation: double-blind study vs. placebo," *Exp Dermatol* 12(3):237-244.

International Search Report mailed on Feb. 10, 2015, for PCT Application No. PCT/IB2014/001741, filed on Apr. 22, 2014, 5 pages.

Jung, K. et al. (Mar. 13, 2006, e-published Feb. 21, 2006). "The antioxidative power AP—A new quantitative time dependent (2D) parameter for the determination of the antioxidant capacity and reactivity of different plants," *Spectrochim Acta A Mol Biomol Spectrosc* 63(4):846-850.

Lee, J.H. et al. (Dec. 2005, e-published Aug. 15, 2005). "The effects of epigallocatechin-3-gallate on extracellular matrix metabolism," *J Dermatol Sci* 40(3):195-204.

Lin, J.Y. et al. (Jun. 2003). "UV photoprotection by combination topical antioxidants vitamin C and vitamin E," *J Am Acad Dermatol* 48(6):866-874.

Lin, F.H. et al. (Oct. 2005). "Ferulic acid stabilizes a solution of vitamins C and E and doubles its photoprotection of skin," *J Invest Dermatol* 125(4):826-832.

Martin, K. et al. (Feb. 2008, e-published Dec. 11, 2007). "Parthenolide-depleted Feverfew (*Tanacetum parthenium*) protects skin from UV irradiation and external aggression," *Arch Dermatol Res* 300(2):69-80.

Matsui, M.S. et al. (Aug. 2009). "Non-sunscreen photoprotection: antioxidants add value to a sunscreen," *J Investig Dermatol Symp Proc* 14(1):56-59.

McDaniel, D.H. et al. (Jan. 2005). "Idebenone: a new antioxidant—Part I. Relative assessment of oxidative stress protection capacity compared to commonly known antioxidants," *J Cosmet Dermatol* 4(1):10-17.

McDaniel, D.H. et al. (Sep. 2005). "Clinical efficacy assessment in photodamaged skin of 0.5% and 1.0% idebenone," *J Cosmet Dermatol* 4(3):167-173.

Mitragotri, S. (Jan. 2013, e-published Aug. 30, 2012). "Devices for overcoming biological barriers: the use of physical forces to disrupt the barriers," *Adv Drug Deilv Rev* 65(1):100-103.

(56) References Cited

OTHER PUBLICATIONS

Mnich, C.D. et al. (Jan. 2009, e-published Jul. 9, 2008). "Green tea extract reduces induction of p53 and apoptosis in UVB-irradiated human skin independent of transcriptional controls," *Exp Dermatol* 18(1):69-77.

Niki, E. (Aug. 15, 2010, e-published Apr. 21, 2010). "Assessment of antioxidant capacity in vitro and in vivo," *Free Radic Biol Med* 49(4):503-515.

Pinnell, S.R. (Jan. 2003). "Cutaneous photodamage, oxidative stress, and topical antioxidant protection," *J Am Acad Dermatol* 48(1):1-19.

Podda, M. et al. (Jan. 1, 1998). "UV-irradiation depletes antioxidants and causes oxidative damage in a model of human skin," *Free Radic Biol Med* 24(1):55-65.

Ponec, M. et al. (Sep. 1997). "The formation of competent barrier lipids in reconstructed human epidermis requires the presence of vitamin C," *J Invest Dermatol* 109(3):348-355.

Pratt, S.G. et al. (Aug. 2006). "Superfoods," Superfoods HealthStyle, located at <http:revolutionarychoices.com/wp-content/uploads/2011/10/Superfoods.pdf>, 4 pages.

Rangarajan, V. et al. (2010). "Topical growth factors for skin rejuvenation" in *Textbook of Skin Aging*, Farage et al, eds., Springer, pp. 1079-1087.

Rawlings, A.V. (Feb. 2012). "Long-standing scientist and ICS editorial board member passes away," *Int J Cosmet Sci* 34(1):1-6.

Rijnkels, J.M. et al. (Feb. 2003). "Photoprotection by antioxidants against UVB-radiation-induced damage in pig skin organ culture," *Radiat Res* 159(2):210-217.

Sauer, R. et al. (Apr. 2007, e-published Apr. 23, 2007). "An updated systematic review of the pharmacology of silymarin," *Forsch Komplementmed* 14(2)70-80.

Shindo, Y. et al. (Mar. 1993). "Antioxidant defense mechanisms in murine epidermis and dermis and their responses to ultraviolet light," *J Invest Dermatol* 100(3):260-265.

Shindo, Y. et al. (Jan. 1994). "Enzymic and non-enzymic antioxidants in epidermis and dermis of human skin," *J Invest Dermatol* 102(10):122-124.

Shindo, Y. et al. (Apr. 1994). "Dose-response effects of acute ultraviolet irradiation on antioxidants and molecular markers of oxidation in murine epidermis and dermis," *J Invest Dermatol* 102(4):470-475.

Singh, R.P. et al. (Aug. 2002). "Flavonoid antioxidant silymarin and skin cancer," *Antioxid Redox Signal* 4(4):655-663.

Sinha, V.R. et al. (Nov. 2000). "Permeation enhancers for transdermal drug delivery," *Drug Dev Ind Pharm* 26(11):1131-1140.

Taungjararuwinai, W.M. et al. (Jul. 2009). "Differential expression of the antioxidant repair enzyme methionine sulfoxide reductase (MSRA and MSRB) in human skin," *Am J Dermatopathol* 31(5):427-431.

Thiele, J.J. et al. (2000). "Antioxidant defense systems in skin" in Cosmeceuticals—Drugs vs. Cosmetics, Elsner et al.,eds., Marcel Dekker, Inc., New York, pp. 145-187.

Thiele, JJ. et al. (Sep.-Oct. 2003). "Impact of ultraviolet radiation and ozone on the transepidermal water loss as a function of skin temperature in hairless mice," *Skin Pharmacol Appl Skin Physiol* 16(5):283-290.

Thiele, J.J. et al. (Oct.-Dec. 2007, e-published Jul. 3, 2007). "Vitamin E in human skin: organ-specific physiology and considerations for its use in dermatology," *Mol Aspects Med* 28(5-60:646-667.

Tournas, J.A. et al. (May 2006). "Ubiquinone, idebenone, and kinetin provide ineffective photoprotection to skin when compared to a topical antioxidant combination of vitamins C and E with ferulic acid," *J Invest Dermatol* 126(5):1185-1187.

Wang, S.Q. et al. (Sep. 2011, e-published May 31, 2011). "Ex vivo evaluation of radical sun protection factor in popular sunscreens with antioxidants," *J Am Acad Dermatol* 65(3):525-530.

Wei, H. et al. (Nov. 2003). "Isoflavone genistein: photoprotection and clinical implications in dermatology," *J Nutr* 133(Suppl 1):3811S-3819S.

Written Opinion mailed on Feb. 10, 2015, for PCT Application No. PCT/IB2014/001741, filed on Apr. 22, 2014, 9 pages.

Zhang, L. et al. (Sep.-Oct. 2009). "Cosmeceuticals and peptides," *Clinics in Dermatology* 27(5):485-494.

\* cited by examiner

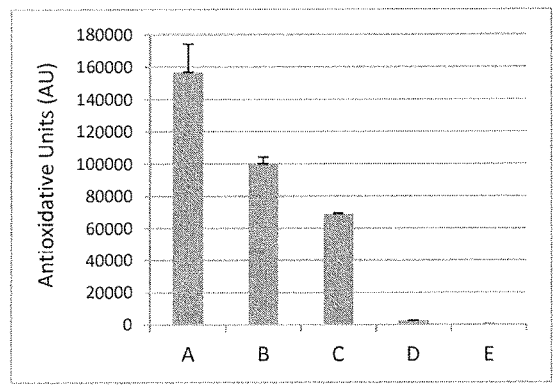 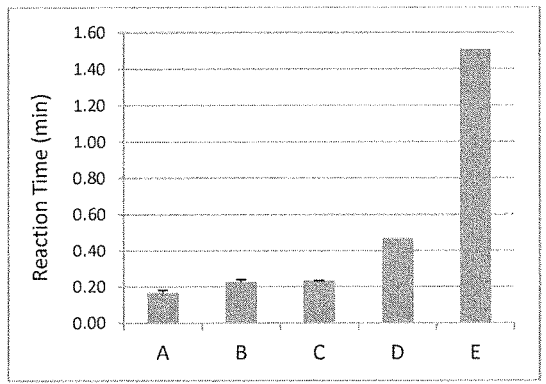
*Figure 1A:* Antioxidant power (mean ± standard deviation)
*Figure 1B:* Antioxidant reaction time (mean ± standard deviation)

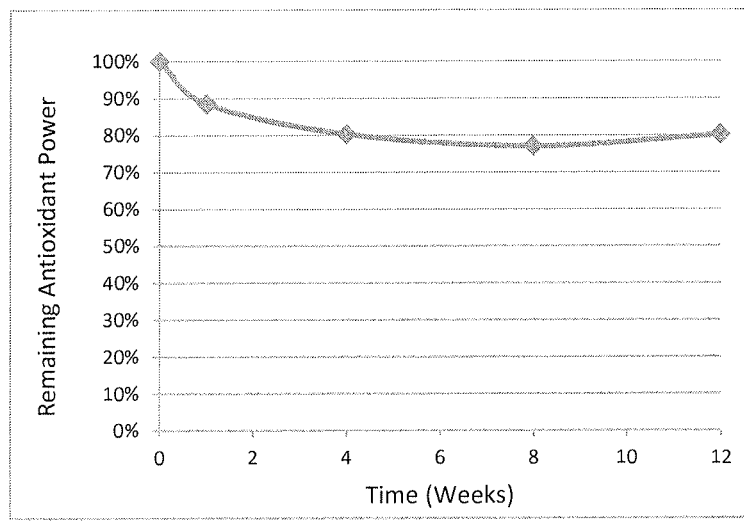
*Figure 2:* Stability antioxidant capacity of Product A over a period of 12 weeks at 40°C

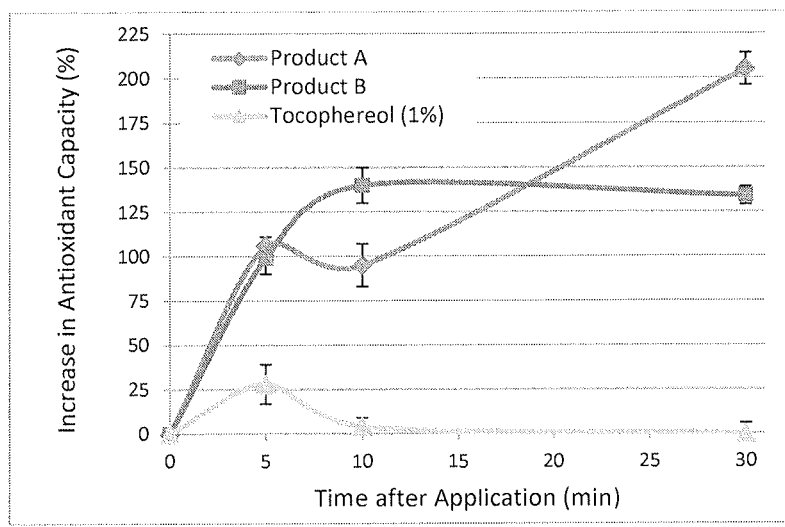
*Figure 3: Skin's antioxidant capacity is enhanced after application of Products A and B*

ANTIOXIDANT COMPOSITIONS AND METHODS OF USING THE SAME

RELATED APPLICATIONS

This application claims priority to U.S. Provisional Application No. 61/814,791, filed Apr. 22, 2013; to U.S. Provisional Application No. 61/830,423, filed Jun. 3, 2013; and to U.S. Provisional Application No. 61/875,294, filed Sep. 9, 2013, each of which is herein incorporated by reference in its entirety.

FIELD OF THE INVENTION

This invention relates generally to stable antioxidant compositions and to methods of using the same.

BACKGROUND OF THE INVENTION

Human skin is a complex organ (the largest human organ) which extends over the entire body. As the outermost organ, the skin forms a protective barrier to protect the body from harm. Skin is subject to abuse from both external and internal factors, which can result in skin aging. Skin aging occurs in two ways: (1) chronological aging (i.e., the natural aging process) and (2) through UV rays in sunlight, which accelerate the natural aging process (i.e., photoaging). Chronological aging may result in thinning, loss of elasticity, and/or general degradation of the skin. By contrast, photoaging, which happened in areas of habitual sun exposure, may result in changes such as elastosis, atrophy, wrinkling, vascular changes (i.e., diffuse erythema, ecchymosis, and telangiectasias), pigmentary changes (i.e., lentigines, freckles, and areas of hypo- and hyper-pigmentation), and/or the development of seborrheic keratosis, actinic keratosis, comedones, and cysts.

While the skin is equipped with natural defenses that help to protect it from damage, these defenses can become overwhelmed, which can lead to skin damage.

Skin appearance and elasticity is a wide spread cosmetic concern. In addition, in recent years, skin protection has also become a great health concern.

Antioxidants are commonly used to improve the therapeutic or cosmetic performance of dermatological and cosmetic formulations. However, in order to be effective, antioxidants must remain in their unoxidized form. As a result, maintenance of antioxidant stability in a formulation suitable for topical administration has often proven to be a challenge.

Thus, a need exists in the art for additional topical compositions having improved and/or superior antioxidant activity that are suitable for topical application and/or administration.

SUMMARY OF THE INVENTION

Provided herein are well-tolerated (i.e., non- to maximal mildly irritating and non-allergenic to skin), stable topical compositions including at least one topically acceptable (i.e., non- to maximal mildly irritating, non-allergenic, non-comedogenic, absorbs into skin within minutes after topical application, feels non- or only a little sticky during topical application, feel non-sticky during topical application, and/or feels non-greasy after absorption into skin after topical application) silicone oil and/or non-silicon oil in combination with Vitamin C (e.g., L-ascorbic acid), Vitamin E (e.g., tocopherol), and one or more polyphenol antioxidants. Such compositions may also include at least one additional antioxidant (e.g., creatine) and/or at least one low molecular weight (i.e., less than 300 g per mol) chromane or chromene derivative with antioxidant properties (e.g., dimethylethoxy chromanol). Preferably, the silicone oil and/or non-silicon oil is present in an amount that is sufficient to prevent degradation of the Vitamin C in the composition, while facilitating the prevention or treatment of oxygen, nitrogen, and/or other radical related skin damage after topical administration. Those skilled in the art will recognize that a "radical", also referred to interchangeably herein as a "free radical" is an atom, molecule, or ion that has unpaired valence electrons. The compositions of the invention are also preferably substantially free of water.

For example, suitable compositions according to the invention may include at least one topically acceptable silicone oil and/or non-silicon oil in combination with Vitamin C, Vitamin E, one or more polyphenol antioxidants, and at least one additional antioxidant; at least one topically acceptable silicone oil and/or non-silicon oil in combination with Vitamin C, Vitamin E, one or more polyphenol antioxidants, at least one additional antioxidant, and at least one low molecular weight chromane or chromene derivative with antioxidant properties; or at least one topically acceptable silicone oil and/or non-silicon oil in combination with Vitamin C, Vitamin E, one or more polyphenol antioxidants, and at least one Vitamin E analog.

Ascorbic acid, also known as Vitamin C, is one of the most popular antioxidants, and this vitamin is known for its general essential role in maintaining health. In dermatology, Vitamin C is known for its implication in collagen synthesis as well as for its antioxidant function, which ultimately helps reduce the expression of skin aging, which is translated into the appearance of fine lines or wrinkles in the skin. Vitamin C also has an anti-tyrosinase effect on the skin, which leads to a skin whitening effect.

Vitamin C is a moderately strong reducing agent, which makes it unstable in aqueous systems, especially at high pHs. It is particularly subject to oxidative degradation, and, in aqueous systems (e.g., water solutions, etc.), ascorbic acid (Vitamin C) is readily degraded into oxidized forms that do not possess antioxidant properties. As a result, it is important to find a non-aqueous system containing silicone oils and/or non-silicon oils which maintains Vitamin C's stability over a prolonged period of time (e.g., from minimally three months up to at least two to four years (or more)).

Vitamin C may be preferentially present in any of the compositions described herein in a micronized form in order to maintain Vitamin C's stability in the formulation. For example, micronized Vitamin C may be present in the composition in an amount between 1 and 30% (as weight percentages) (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30%).

Preferentially, the Vitamin C used in the antioxidant composition of the invention is micronized using methods known to those familiar in the art of micronizing chemical granules into particles less than 25 μm in diameter (i.e., less than 24, 23, 22, 21, 20, 19, 18, 17, 16, 15, 14, 13, 12, 11, 10, 9, 8, 7, 6, 5, 4, 3, 2, or 1 μm in diameter). By way of non-limiting example, the Vitamin C may be micronized by jet milling, ball milling, and/or any other method(s) commonly used in the relevant art.

In any of the antioxidant compositions of the invention, at least one pharmaceutically acceptable silicone oil and/or non-silicon oil is used in order to inhibit the degradation of Vitamin C (and/or any other component of the antioxidant composition described herein). (See, e.g., U.S. Pat. No. 6,194,452, which is herein incorporated by reference). Silicone oils are non-polar compounds that may be volatile or non-volatile. Suitable silicone oils for use in the antioxidant compositions of the invention may include, but are not limited to, cyclomethicones (volatile silicones), linear silicones, dimethylpolysiloxane, dimethicone copolyols, silicone glycols, aminofunctional silicones, polymeric silicones, silicone waxes (e.g., high weight dimethicones an silicone derivative waxes). (See U.S. Pat. No. RE38,623, which is herein incorporated by reference in its entirety). Suitable oils other than silicone oils may include, but are not limited to, hydrogenated polyisobutene, medical grade (e.g., USP) of mineral oil, and/or medical grade of petrolatum.

The use of at least one silicone oil or non-silicon oil may help to avoid or reduce irritancy of the antioxidant compositions of the invention. Moreover, the one or more silicone oil or non-silicone oil are preferably non-reactive (i.e., chemically inert to antioxidants and free radicals) and have relatively low surface tensions, which allow them to form a physical barrier coating around the Vitamin C particle (e.g., crystal of Vitamin C, micronized Vitamin C), thereby reducing exposure to air and moisture, and, as a result, minimizing its rate of oxidation and thereby improving it stability.

Vitamin E (i.e., tocopherol) may be present in any of the compositions described herein in an amount between 0.1 and 5% (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5%).

Tocopherols and tocotrienols, which are collectively known as Vitamin E or "tocols", are fat-soluble biological membrane components that are structurally related, as each have the same aromatic chromanol "head". Tocopherols may include alpha, beta, delta, and gamma tocopherols or derivatives thereof. Tocotrienols may include alpha, beta, delta, and gamma tocotrienols or derivatives thereof.

Along with Vitamin C, Vitamin E is one of the most important dietary antioxidants. In addition, it may also have other anti-atherogenic properties. When Vitamin E works as an antioxidant, it is oxidized to harmful α-tocopherol radical, which needs to be reduced back to α-tocopherol. Vitamin C is able to reduce α-tocopherol radical back to α-tocopherol. (See U.S. Pat. No. 6,805,880, which is herein incorporated by reference in its entirety).

Creatine may be present in any of the compositions described herein in an amount between 0.1 and 5% (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5%).

Creatine (also known as N-(aminoiminomethyl)-N-methylglycine; methylglycosamine or N-methyl-guanido acetic acid) is a compound that is naturally occurring and is found in the mammalian brain and other excitable tissues (i.e., skeletal muscles, retina, and heart). Creatine is an excellent stimulant of oxidative phosphorylation and high energy production, and creatine compounds may preserve tissue by boosting up energy reserves in the skin and also by arresting mechanisms involved in oxidative stress and cell death. (See US Patent Publication 20050286158, which is herein incorporated by reference).

The creatine kinase system is involved in energy buffering/energy transport activities and in regulating ADP and ATP levels intracellularly as well as ADP/ATP ratios. The creating content and efficiency of the creatine kinase system decreases with aging. It has been shown the modulation of the creatine kinase system can result in minimized rate of production of molecules associated with oxidative damage. (See US Patent Publication 20050286158, which is herein incorporated by reference in its entirety). This minimization, combined with the energy boosting effects, could slow tissue damage during aging and/or exposure to insults. Thus, creatine and/or creatine analogs that modify the rate of ATP synthesis through creatine kinase could sustain energy production, mitochondrial function, and/or protect against free radical production. (See id.).

The low molecular weight chromane (i.e., dimethylmethoxyl chromanol) or chromene derivative with antioxidant properties may be present in any of the compositions described herein an amount between 0.01 and 1% (e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1%).

In various embodiments, the one or more polyphenol antioxidants is selected from the group consisting of flavonoids; flavonols; flavones; catechins; flavanones; anthocyanidins; isoflavonoids; and/or plant, vegetable, or fruit extracts such as, but not limited to, those obtained from green tree leaves, milk thistle, soybeans, wine grapes and their seeds, acai berry, coffee berry, feverfew, pomegranate, tropical ferns, turmeric, and witch hazel. For example, the one or more polyphenol antioxidants may be epigallocatechin gallate (EGCG), which may be present in an amount between 0.01 and 0.5% (e.g., 0.01, 0.02, 0.03, 0.04, 0.05, 0.06, 0.07, 0.08, 0.09, 0.1, 0.2, 0.3, 0.4, or 0.5%).

In one embodiment, the antioxidant composition according to the invention contains at least one topically acceptable silicone or oil and Vitamin C present in an amount between 1 and 30%, Vitamin E present in an amount between 0.1 and 5%, epigallocatechin gallate (EGCG) present in an amount between 0.01 and 0.5%, the low molecular weight chromane derivative with antioxidant properties dimethylmethoxy chromanol present in an amount between 0.01 and 1%; and/or creatine present in an amount between 0.1 and 5%.

In other embodiments, the antioxidant composition contains at least one topically acceptable silicone oil and/or non-silicon oil and Vitamin C present in an amount between 1 and 30%, Vitamin E present in an amount between 0.1 and 5%, and epigallocatechin gallate (EGCG) present in an amount between 0.01 and 0.5%; at least one topically acceptable silicone oil and/or non-silicon oil and Vitamin C present in an amount between 1 and 30%, Vitamin E present in an amount between 0.1 and 5%, epigallocatechin gallate (EGCG) present in an amount between 0.01 and 0.5%, and the low molecular weight chromane derivative with antioxidant properties dimethylmethoxy chromanol present in an amount between 0.01 and 1%; or at least one topically acceptable silicone oil and/or non-silicon oil and Vitamin C present in an amount between 1 and 30%, Vitamin E present in an amount between 0.1 and 5%, epigallocatechin gallate (EGCG) present in an amount between 0.01 and 0.5%, and creatine present in an amount between 0.1 and 5%.

The antioxidant compositions of the invention may also contain one or more additional carriers or excipients suitable for topical administration and/or subcutaneous administration.

In some embodiments, the compositions may also contain one or more additional active ingredients.

Also provided are pharmaceutical and/or cosmetic compositions containing any of the compositions described herein along with one or more pharmaceutically and/or cosmetically acceptable carriers.

Any of the compositions described herein can also be included in kits. Such kits contain, in one or more containers, these compositions as well as instructions for use.

Also provided are methods for modifying free radical damage to skin by administering any of the compositions of the invention to a patient in an amount sufficient to treat and/or prevent free radical damage to skin.

The invention also provides methods of treating, alleviating, improving and/or ameliorating a symptom, condition, disorder, or disease (e.g., of the skin) associated with free radicals, the method comprising administering an effective amount of any of the composition of the invention to a patient in need thereof. For example, the symptom, condition, disorder, or disease associated with free radicals is selected from the group consisting of sun induced skin damage, skin aging, inflammatory skin diseases or disorders, degenerative skin diseases or disorders, and/or cancer (e.g., skin cancer). Diseases and disorders of skin that also may result from radical damage include, but are not limited to skin cancer, skin irritation or inflammation, dermatitis, allergy, psoriasis, acne, eczema, and rosacea. In addition, diseases and disorders of skin may result from radical damage caused by visible light exposure, UV-radiation exposure, IR-radiation exposure, X-ray radiation exposure, smoking, air pollution, nutritional deficit or imbalance, and certain medications causing free radicals.

In any of the methods described herein, treating, alleviating, improving and/or ameliorating the symptom neutralizes free radicals. These methods may involve the repeated topical and/or subcutaneous administration of the composition to the individual (e.g., the patient). For example, any of the compositions of the invention can be administered to the patient at least once or twice a day for at least 30 days or more.

Also provided are methods for modifying free radical damage to skin by administering an effective amount of any of the compositions of the invention to the skin of a patient. In such methods, the effective amount is sufficient to treat, prevent, improve, treat and prevent, treat and improve, prevent and treat, prevent and improve, and/or treat and prevent and improve or otherwise modify free radical damage to the skin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 1A-1B show the antioxidant power (FIG. 1A) and reaction time (FIG. 1B) of the five different test products. The results shown are the average (±standard deviation) of two to three batches. Product A represents an example of a composition according to this invention, whereas Product B, Product C, Product D, and Product E are not examples of compositions according to this invention.

FIG. 2 shows the stability of the antioxidant capacity of Product A (which represents an example of a composition according to this invention) over a period of 12 weeks at 40° C. as determined by ESR.

FIG. 3 shows that the skin's antioxidant capacity is enhanced after application of Products A (which represents an example of a composition according to this invention) and B (which does not represent an example of a composition according to this invention) as determined by ESR. One single lot was tested per product. Data is shown as mean with standard deviation (n=4).

DETAILED DESCRIPTION OF THE INVENTION

Figure 4:
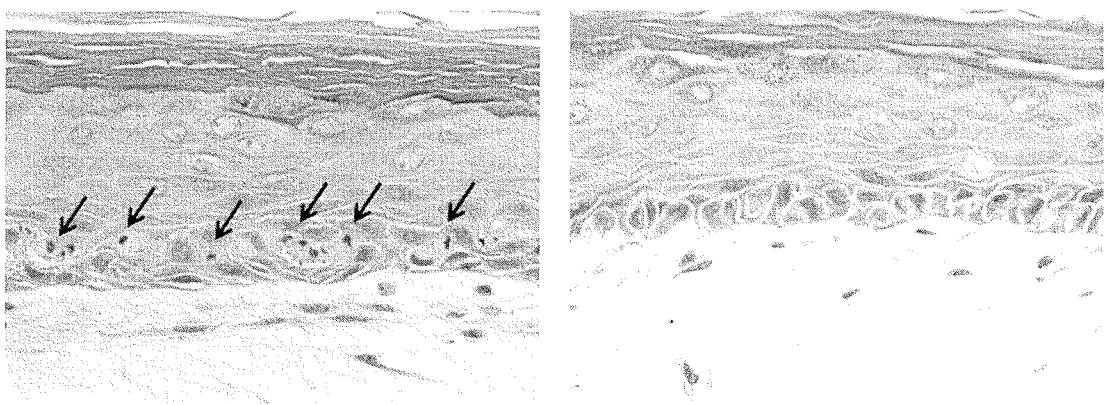
FIG. 4 shows H&E staining of a full-thickness human skin model 24 h after irradiation with solar simulated UVB-light in untreated skin (left), and Product A treated skin (right) at 40× magnification. The sunburn cells, which are characterized by their phenotype (pyknotic nuclei and eosinophilic cytoplasm), are marked with short arrows.

The present invention will be better understood from the following description.

In this specification where reference is made to particular features of the invention it is to be understood that the disclosure of the invention in this specification includes all appropriate combinations of such particular features. The embodiments disclosed in this specification are exemplary and do not limit the invention. As used in this specification, the singular forms "a", "an", and "the" include plural reference unless the context clearly dictates otherwise. The terms "comprises" and "contains" and grammatical equivalents thereof are used in this specification to mean that, in addition to the features specifically identified, other features are optionally present. The term "at least" followed by a number is used herein to denote the start of a range beginning with that number.

While the specification concludes with the claims particularly pointing and distinctly claiming the invention, it is believed that the present invention will be better understood from the following description. The terms "having" and "including" are to be construed as open-ended unless the context suggests otherwise.

The present invention relates to non- to maximal mildly irritating, stable topical compositions including at least one topically acceptable silicone oil or non-silicone oil in combination with an acceptable, Vitamin C (e.g., L-ascorbic acid), Vitamin E (e.g., α-tocopherol) and one or more polyphenol antioxidants. The silicone oil or non-silicon oil is present in these compositions an amount sufficient to prevent degradation of the Vitamin C in the composition, while facilitating the prevention or treatment of oxygen, nitrogen and other radical (also referred to as free radical) related skin damage. Any of the compositions described herein may also include at least one additional antioxidant, such as, for example, creatine and/or at least one low molecular weight (i.e., less than 300 g per mol) chromane or chromene derivative with antioxidant properties, such as, for example, dimethylmethoxychromanol. Preferably, these compositions are free of water or substantially free of water (i.e., >95%, >96%, >97%, >98%, or >99% free of water).

The present invention also relates to methods for modifying free radical damage to skin by administering the above composition in an effective amount sufficient to treat and/or prevent free radical damage to skin.

Free Radicals and Oxidative Stress

An equilibrium failure between the creation and elimination of reactive oxygen species (ROS) and reactive nitrogen species (RNS) and other free radicals leads to oxidative stress. Exemplary ROS and RNS are shown in Table 1.

TABLE 1

| ReactiveOxygen Species (ROS) | Symbol | ReactiveNitrogen Species (RNS) | Symbol |
|---|---|---|---|
| Hydroxyl | OH• | Nitrous oxide | NO• |
| Superoxyde | $O_2^{•-}$ | Peroxynitrate | OONO$^-$ |
| Nitric Oxide | NO• | Peroxynitrous acid | ONOOH |
| Peroxyl | RO$_2$• | Nitroxyl anion | NO$^-$ |
| Lipid peroxyl | LOO• | Nitrogen dioxide | NO•$_2$ |
| Peroxynitrate | ONOO$^-$ | Dinitrogen trioxide | $N_2O_3$ |
| Hydrogen Peroxide | $H_2O_2$ | Nitrous add | $HNO_2$ |
| Singlet Oxygen | $^1O_2$ | Nitryl chloride | $NO_2Cl$ |
| Hypochloric acid | HOCl | Nitrosyl cation | NO$^+$ |

The skin is permanently exposed to various intrinsic (e.g., disease inflammation, autoimmune reactions, disregulation of metabolism, ischemia, etc.) and extrinsic (e.g., microbial organism, electromagnetic radiation, mechanical stress, thermal stress, chemical stress, etc.) influences. As a result of these influences, various free radicals are generated, including, for example, hydroxyl radical (.OH); lipid alkyl radical (L.); lipid alkoxyl radical (LO.); lipid-peroxyl radical (LOO.); superoxide anion radical ($O_2^-$.); singlet oxygen ($^1O_2$); nitric oxide (NO); ascorbyl radical; tocopheroxyl radical; melanin radical; and many other radicals, including those listed in Table 1.

A free radical is an atom, molecule, or ion that has unpaired valence electrons that make it chemically reactive. Radicals seek to receive or release electrons in order to achieve a more stable configuration, and this process can damage any molecules within cells. By way of non-limiting example, the formation of free radicals can be the result of exposure to sun light, visible light, UV light, IR-light, ionizing radiation (i.e., X-rays), smoking, and/or air pollution. Free radical formation can also result from inflammation and metabolism or certain diseases such as cancer, skin irritation or inflammation, dermatitis, allergy, psoriasis, acne, eczema, and rosacea.

Oxidative stress can also occur within the mitochondria (known as "mitochondrial oxidative stress"), where it can adversely impact redox signaling and/or lead to mitochondrial dysfunction and/or apoptosis/necrosis.

Oxidative stress is known to play a role in disease and aging. (See Krutmann et al., J. Investigative Dermatology Symposium Proceedings 14:44-49 (2009); Berneburg M. et al., J. Invest. Dermatol. 125:213-20 (2005)). For example, solar UV-radiation (UVR) induced skin damage may include acute reactions, such as erythema and edema, followed by exfoliation, tanning and epidermal thickening. Premature skin aging (photoaging) and photocarcinogenesis are the consequences of chronic UVR exposure.

Several steps lead to the formation of ROS during UVR exposure, which represents the best characterized source of oxidative stress in skin. (See Thiele et al., Oxidants and Antioxidants in Cutaneous Biology, Inc. Burg ed., Current Problem in Dermatology 29 (Karger: Basel 2001). The cascade of ROS formation is initiated by UVR-absorption, predominantly in the UVA region, of endogenous or exogenous chromophores present in the skin. Of the many skin constituents capable of absorbing UVA, trans-urocanic acid, melanins, flavins, porphyrins, quinones, protein bound tryptophan or advanced glycation end products are believed to be relevant photosensitizers initiating the ROS formation cascade. Following their formation, ROS species including $^1O_2$, $.O_2^-$, .OH, $H_2O_2$ react with an array of skin biomolecules including lipids, proteins, carbohydrates and DNA. For instance, (poly)unsaturated lipids (LH) may react with ROS forming lipid peroxyl (LOO.) and alkoxyl radicals (LO.), which may initiate a chain-propagating autocatalytic reaction. Further, ROS cause modifications of amino acids of proteins resulting in functional changes of structural or enzymatic proteins. Besides a multitude of ROS mediated DNA damage, reaction of singlet oxygen with DNA results in the formation of 8-hydroxy-deoxyguanosine. Since DNA absorbs strongly in the UVB region and is only a weak chromophore in the UVA region, UVB is largely considered as a direct, ROS-independent inducer of DNA damage. (See Chang et al., Free Radic Res 37:655-63 (2003)). UVB absorption of DNA leads to major base modifications such as pyrimidine dimer or (6-4) photoadduct formation, and these modifications, together with indirect DNA damage induced by ROS, are involved in solar genotoxicity.

Skin Aging

All terms such as "skin aging", "signs of skin aging", "topical application", and the like are used in the sense in which they are generally and widely used in the art of developing, testing and marketing cosmetic and personal care products, as well as for medicaments which are indicated for skin aging (e.g., cream with tretinoin).

Skin aging is classified into intrinsic aging and extrinsic aging depending on its cause. Intrinsic aging is a process by which the skin structure and the physiological functions of the skin deteriorate regardless of environmental changes as a human gets older. Extrinsic aging is caused by continuous exposure to external environment such as sunlight and air pollutants. Especially, skin aging caused by sun light is called photoaging. Ultraviolet (UV) light from the sun is the main cause of the physiological and morphological changes in aged skin.

Continuous exposure to the sun is the main cause of extrinsic aging of skin. The UV component of sunlight, particularly UVA and UVB, is generally believed to be the principal causative agent in this process called photoaging. The extent of UV exposure required to cause "photoaging" is not currently known, although the amount sufficient to cause erythema (reddening, commonly described as sunburn) in human skin is quantified as the "minimal erythema dose" (MED) from a given UV light source. Repeated exposure to sunlight UV at levels that cause erythema and tanning are, nevertheless, commonly associated with photoaging.

There is a difference between the physiology of intrinsically-aged (i.e., chronologically-aged) skin in comparison with that of photoaged skin. Chronologically-aged skin typically maintains a smooth and unblemished appearance, in comparison with the leathery, blotchy, and often deep wrinkling of photoaged skin. Photoaging is characterized clinically by coarseness, wrinkles, mottled pigmentation, sallowness, laxity, telangiectasia, lentigines, purpura and relative ease of bruising, atrophy, depigmented areas, eventually premalignant, and ultimately malignant neoplasm (i.e., abnormal mass of tissue as a result of neoplasia, which is the abnormal proliferation of cells). Photoaging commonly occurs in skin that is generally exposed to sunlight such as the face, ears, bald areas of the scalp, neck, décolleté, forearms, and hands.

"Signs of skin aging" include, but are not limited to, all outward visibly and tactilely perceptible manifestations as well as any other macro or micro effects due to skin aging. Such signs may be induced or caused by intrinsic factors (showing as chronological aged skin) and extrinsic factors (showing as environmental skin damage including but not limited photo-aged skin). These signs may result from processes which include, but are not limited to, the development of textural discontinuities such as wrinkles and coarse deep wrinkles, fine or skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

Antioxidants

To counteract ROS-, RNS-, and other radical induced oxidative stress, the skin is equipped with a variety of antioxidants forming an antioxidant network, which intervenes at different levels of oxidative processes by scavenging and removing free radicals or oxidatively damaged biomolecules. (See Thiele et al., Antioxidant defense systems in skin; In Elsner et al., eds., Cosmeceuticals—Drugs vs. Cosmetics (Dekker: New York, 2000) 145-87). Antioxidants are a heterogeneous class of molecules that neutralize free radicals and can stop radical chain reactions. (See Herrling et al., Int. J. Cosm. Sci 1-6 (2012), which is herein incorporated by reference in its entirety; see also Dreher et al, "Antioxidants", Chapter 13 in Textbook of Cosmetic Dermatology, 2010, $4^{th}$ edition, pages 115-122). Antioxidants function by preventing the free radicals from causing premature skin aging.

The skin possesses enzymatic and nonenzymatic antioxidants, which form an interactive and cooperative antioxidant defense network that functions by scavenging and removing free radicals or oxidatively damaged biomolecules. (See Dreher et al., "Antioxidants", Chapter 13 in Textbook of Cosmetic Dermatology, 2010, $4^{th}$ edition, at page 115). Moreover, the skin also possesses mechanisms of "antioxidant repair" that are able to reverse oxidatively damaged proteins. (See Dreher et al., "Antioxidants", Chapter 13 in Textbook of Cosmetic Dermatology, at page 116, $2^{nd}$ col.).

Antioxidants enzymes such as superoxide dismutases (SOD), catalase, glutathione reductase and peroxidase, glutathion-S-transferase and thioredoxin reductase and peroxidase interact with low molecular weight lipophilic antioxidants including Vitamin E homologues (i.e., tocopherols and tocotrienols) and ubiquinols (i.e., coenzyme Q) as well as hydrophilic antioxidants such as Vitamin C (i.e., ascorbic acid or ascorbate) and glutathione (i.e., GSH).

Carotenoids, retinoids and uric acid, which also possess antioxidant activity, were further detected in skin. Their role within the cutaneous antioxidant network is, however, less clear.

In addition to its antioxidant activity, L-ascorbic acid acts as cofactor in a multitude of metabolic processes involved in skin formation. For example, it is required in hydroxylation reactions during collagen synthesis to form connective tissue (see Davidson et al, J Biol Chem 272:345-52 (1997)) and participates in biosynthesis of epidermal barrier lipids (See Ponec et al., J Invest Dermatol 109:348-55 (1997)).

α-tocopherol, the predominant Vitamin E homologue in skin, is known to efficiently scavenge lipid peroxyl and alkoxyl radicals by intercepting lipid chain propagation, which results in the formation of the meta-stable tocopheroxyl radical. This radical formed then either reacts with another lipid radical leading to α-tocopherol consumption, or abstracts a hydrogen atom from polyunsaturated lipids to give α-tocopherol and lipid radical. In the latter case, which preferentially occurs at low lipid radical concentration, the lipid radical may later react with oxygen to form a lipid peroxyl radical. This reaction consequently induces the α-tocopherol-mediated lipid peroxidation chain reaction. Formation of one molecule of α-tocopherol radical results in the formation of many lipid hydroperoxides. However, as demonstrated in vitro in lipid and cellular systems, when ascorbic acid or ubiquinol are present, the tocopheroxyl radical is rapidly reduced, thereby regenerating α-tocopherol. As a result, the α-tocopherol mediated lipid peroxidation chain reaction is thereby terminated.

In addition, due to its high reduction potential, ascorbic acid is also an efficient scavenger of a series of ROS such as superoxide anion radicals, hydroxyl radicals, singlet oxygen as well as water soluble peroxyl radicals. The resulting ascorbic acid radical can be either recycled to ascorbic acid by co-antioxidants such as glutathione or can be further oxidized to dehydroascorbic acid and irreversibly decomposed, respectively.

Glutathione also reacts with singlet oxygen, superoxide anion radicals and hydroxyl radicals resulting in the formation of the thiyl radical GS. and subsequently glutathione disulfide GSSG. The latter can be recycled to GSH by the NAD(P)H-dependent enzyme glutathione reductase. GSH further acts as a cofactor for numerous reducing enzymes, among them glutathion peroxidases. Glutathion peroxidase is an intracellular selenoenzyme utilizing lipid peroxides as substrate and converting them to hydroxy fatty acids. Glutathion peroxidase also catalyzes the conversion of $H_2O_2$ into water and oxygen. Less reactive $H_2O_2$ is produced by superoxide dismutase catalyzing the dismutation reaction of superoxide anion radicals. Superoxide dismutase is present in skin as Cu/Zn-SOD and Mn-SOD. GSH is likewise used by glutathion-S-transferases, which catalyze the conjugation of GSH to a variety of electrophils including oxidized lipids, DNA and other products generated by ROS-induced damage to these skin biomolecules. Glutathion-S-transferases therefore play an important role in detoxifying products of oxidative stress.

Moreover, skin also contains catalase, which similar to glutathion peroxidase, eliminates $H_2O_2$. However, catalase contributes to scavenging $H_2O_2$ differently than glutathione peroxidase with respect to its cellular distribution, enzyme stability and reaction rate. The enzymatic activity of catalase is much higher than that of glutathione peroxidase in human epidermis. (See Shindo et al, J. Invest Dermatol 102:122-24 (1994)).

Besides GSH-peroxidase, skin contains a further selenium dependent enzyme, thioredoxin reductase. (See Schallreuter et al, J. Photochem Photobiol B 64:179-84 (1994)). Thioredoxin reductase together with its electron acceptor thioredoxin and thioredoxin peroxidase participates similarly as the enzymic thiol redox couple GSH reductase/peroxidase in the cutaneous $H_2O_2$ turnover.

Along with skin's "interceptive" antioxidant network that scavenge ROS and RNS, the skin also possesses mechanisms of "antioxidant repair" that are able to reverse oxidatively damaged proteins. (See Taungjaruwinai et al, Am J Dermatopathol 31:427-31 (2009)).

In general, non-enzymatic antioxidant concentrations as well as enzymatic antioxidant activities are significantly higher in the epidermis as compared to the dermis, which probably reflects the fact that epidermis is directly exposed to various exogenous sources of oxidative stress and might have evolved to possess a more pronounced antioxidant defense capacity than dermis in order to best maintain the redox balance in skin. On a molar basis, hydrophilic non-enzymatic antioxidants including L-ascorbic acid, GSH and uric acid appear to be the predominant antioxidants in human skin. Their dermal and epidermal overall concentrations are approximately more than 10 to 100 fold greater than found for Vitamin E or ubiquinol/ubiquinone.

Interestingly, in contrast to uric acid, GSH, and ubiquinol, ascorbic acid and the Vitamin E homologues cannot be synthesized by humans and must be taken up by the diet. Consequently, the skin's antioxidant defense may be at least partially influenced by nutritive factors. Knowledge of ascorbic acid's and Vitamin E's physiological regulation in skin is only recently emerging.

Numerous studies documented the effects of UVR or ozone on cutaneous antioxidants after acute or chronic exposure using different animal models; whereas fewer human studies exist investigating the mechanisms and consequences of such effects. (See Thiele et al., Antioxidant defense systems in skin, In Elsner et al., eds. Cosmeceuticals—Drugs vs. Cosmetics (Dekker: New York 2000), 145-87). In particular, the antioxidants contained in the stratum corneum were demonstrated to be susceptible to UVR. The high susceptibility of stratum corneum Vitamin E to UVR may be, at least in part, due to a lack of co-antioxidants in the outermost skin layer. Additionally, ascorbic acid, the major hydrophilic co-antioxidant that is also capable of recycling photooxidized α-tocopherol, is present at lower levels in human stratum corneum than in other skin tissues. Hydrophilic antioxidants have also been shown to be sensitive to UVR. Direct depletion of α-tocopherol and formation of its radical may further affect these endogenous antioxidant pools. However, ascorbic and uric acid appear to be less susceptible to solar simulated UVR than α-tocopherol or ubiquinol-10 as was demonstrated with cultured human skin models. (See Podda et al, Free Radic Biol Med 24:55-65 (1998)). In full thickness epidermis of hairless mice, however, ascorbic acid was depleted at lower solar simulated UV-doses than those needed to deplete lipophilic antioxidants or GSH. (See Shindo et al., J Invest Dermatol 100:260-65 (1993)). In another study, murine epidermal GSH levels were significantly depleted within minutes after UVB exposure but returned to normal levels after half an hour. (See Connor et al., Photochem Photobiol 46:239-45 (1987)). Moreover, exposures of hairless mice to solar simulated UVR demonstrated that dermal and epidermal catalase is more susceptible to photo-inactivation than superoxide dismutase, and far more than GSH-peroxidase and GSSG-reductase. (See Shindo et al., J. Invest Dermatol 100:260-65 (1993); Shindo et al., J Invest Dermatol 102: 470-72 (1994)).

The effects of the air pollutant ozone on skin antioxidants have also been reported. (See Thiele et al., Antioxidant defense systems in skin, In Elsner et al., eds, Cosmeceuticals—Drugs vs. Cosmetics (Dekker: New York, 2000) 145-87; Thiele et al., Oxidants and Antioxidants in Cutaneous Biology, In Burg, ed. Current Problem in Dermatology 29 (Karger: Basel 2001)). Similarly, as found for UVR exposure, the stratum corneum is the most susceptible skin layer for ozone-induced depletion of lipophilic and hydrophilic antioxidants, which was demonstrated using hairless mice. Ozone itself is too reactive to penetrate deeply into the skin and reacts therefore predominantly with the skin barrier lipids and proteins in the outermost epidermis. Comparison of transepidermal water loss changes detected in hairless mice after exposure to either solar simulated UVR or repetitive high doses of ozone indicated that in skin, UVR is a physiologically much more relevant source of oxidative stress than ozone. (See Thiele et al., Skin Pharmacol Appl Skin Physiol 16:283-90 (2003)).

Apart from using sunscreens to diminish the intensity of UVR reaching the skin, supplementation of the skin with topically applied antioxidants and thereby strengthening its antioxidative capacity is an established approach in limiting ROS-induced skin damage. (See Thiele et al., Antioxidant defense systems in skin, In Elsner et al., eds, Cosmeceuticals—Drugs vs. Cosmetics (Dekker: New York, 2000) 145-87; Thiele et al., Oxidants and Antioxidants in Cutaneous Biology, In Burg, ed. Current Problem in Dermatology 29 (Karger: Basel 2001); Pinnell, J Am Acad Dermatol 48:1-19 (2003)). Oral supplementation of antioxidants, is another promising strategy to prevent cutaneous photodamage. (See Fuchs, Free Radic Biol Med 25:848-73 (1998); Boelsma et al., Am J Clin Netr 73:853-64 (2001); Bialy et al., Dermatol Surg 28:1143-52 (2002)). Topical application of antioxidants provides an efficient means of increasing antioxidant tissue levels in human epidermis. As the most susceptible skin layer for UVR- and ozone-induced depletion of cutaneous antioxidants, the stratum corneum may particularly benefit from an increased antioxidant capacity due to topical supplementation.

However, the antioxidant defense in cutaneous tissues can be overwhelmed by an increased or prolonged exposure to exogenous sources of oxidative stress, which can lead to skin damage. Causes of premature skin aging can include, for example, oxidative stress (e.g., external oxidative stress and/or internal oxidative stress). External oxidative stress may be the result of UV light, cigarette smoke, ozone, and/or air pollution, which contribute to free radical formation. Internal oxidative stress is the result of metabolic energy processes, which leads to free radical formation.

Both endogenously produced and UV-generated free radicals in the skin can damage the skin, can lead to photoaging, and can play a role in the development of skin cancer. (See Chen et al., Photodermatology, Photoimmunology & Photomedicine 28:228-34 (2012) (incorporated herein by reference in its entirety)). For example, the exposure of the skin to solar ultraviolet radiation (UVR) and air pollutants results in the formation of reactive oxygen species (ROS) and other free radicals including reactive nitrogen species (RNS). See also Dreher et al., "Antioxidants", Chapter 13 in Textbook of Cosmetic Dermatology, which is incorporated herein by reference in its entirety). These ROS and RNS may then react with biomolecules in the skin. (See id.).

Accordingly, supplemental administration of one or more antioxidants is often required to combat the harmful effects of free radicals in and on the skin.

Vitamin E

The photoprotective effects of Vitamin E (α-tocopherol) have been studied extensively. Most studies were performed in animals, and several studies exist investigating the photoprotective effects of topically applied Vitamin E also in humans. (See Thiele et al., Antioxidant defense systems in skin, In Elsner et al., eds, Cosmeceuticals—Drugs vs. Cosmetics (Dekker: New York, 2000) 145-87; Thiele et al., Oxidants and Antioxidants in Cutaneous Biology, In Burg, ed. Current Problem in Dermatology 29 (Karger: Basel 2001); Thiele et al., Mol Aspects Med 28:646-67 (2007)). Significantly reduced acute skin responses, such as erythema and edema, sunburn cell formation, lipid peroxidation, DNA adduct formation, immunosuppression as well as UVA-induced binding of photosensitizers was demonstrated when Vitamin E was applied before UVR exposure. As shown in animal studies, skin wrinkling and skin tumor incidence due to chronic UVR exposure seem also to be diminished by topical Vitamin E. A human study proved that an alcoholic lotion containing 2% α-tocopherol significantly diminished the erythemal responses when applied 30 min before UVR exposure at a dose of 2 mg cm$^{-2}$ as assessed by measuring skin redness and dermal blood flow. (See Dreher et al., Br J Dermatol 139:332-39 (1998)). Since the lotion had no sunscreening properties, the observed photoprotective effect might be attributed to the antioxidant properties of α-tocopherol. However, the photoprotective mechanism of action of α-tocopherol is still subject of debate, since investigations on the UVB-induced photooxidation of α-tocopherol in liposomes indicated that α-tocopherol might also act as a sunscreen. (See Kramer et al., Chem Res Toxicol 10:219-24 (1997)).

Diverse Vitamin E esters, in particular Vitamin E acetate, were also shown to be promising agents in reducing UVR-induced skin damage. Their photoprotective effects might be less pronounced as compared to Vitamin E. Moreover, some studies failed to detect photoprotection provided by Vitamin E esters. Vitamin E esters need to be hydrolyzed during skin absorption to show antioxidant activity. For instance, bioconversion of Vitamin E acetate into α-tocopherol, its active antioxidative form, seems slow and occurs only to some extent. There is evidence that Vitamin E acetate is not hydrolyzed in the stratum corneum and that its bioconversion into α-tocopherol only occurs after penetration beyond the stratum corneum into the nucleated epidermis. (See Baschong et al., J Cosmet Sci 52:155-61 (2001)).

Consequently, the controversial observations of photoprotective effects of topically applied Vitamin E acetate may be explained by a limited bioavailability of the active, ester-cleaved form during oxidative stress at the site of action. Intriguingly, the bioconversion of Vitamin E acetate into its active form may be enhanced when skin is exposed to sun, possibly by an UVB dependent increase in esterase activity as demonstrated in murine epidermis. (See Kramer-Stickland et al., J Invest Dermatol 111:302-7 (1998)).

Vitamin C

Few studies investigated the photoprotective effects of topical Vitamin C (ascorbic acid). Using a porcine skin model, it was demonstrated that topically applied Vitamin C protects from UVB-induced erythema and sunburn cell formation when formulated at high concentrations (i.e., 15%) in an appropriate vehicle (i.e., aqueous solution with 15% ethanol adjusted to pH 3.2). (See Darr et al., Br J Dermatol 127:247-53 (1992); Lin et al., J Am Acad Dermatol 48:866-74 (2003)). In a human study, however, a hydroalcoholic lotion with 5% Vitamin C was unable to induce any significant photoprotective effects when applied once 30 minutes before irradiation at a dose of 2 mg cm$^{-2}$. (See Dreher et al., Br J Dermatol 139:332-39 (1998)). Besides differences between pig and human skin responses, differences in Vitamin C concentration, amount of formulation applied, vehicle composition as well as other experimental parameters may explain this difference in photoprotective efficacy of the Vitamin C formulations.

Vitamin C is easily oxidized, which makes the development of a stable formulation challenging. Vitamin C can be protected from degradation to some extent at low pH or by appropriate, sophisticated vehicles such as emulsions. (See Gallarate et al., Int J Pharm 188:233-41 (1999)). Furthermore, esterified derivatives such as ascorbyl palmitate or tetra-isopalmitate, magnesium or sodium ascorbyl phosphate, and aminopropyl ascorbyl phosphate are more stable and seem therefore promising alternatives to Vitamin C. (See Farris, Dermatol Surg 31:814-7 (2005)). As described for Vitamin E esters, some of these compounds must be hydrolyzed to Vitamin C to manifest antioxidant properties.

Vitamin C does not act as sunscreen; nor does it absorb UVA. In addition to its antioxidant properties, Vitamin C participates in synthesis of collagen as co-factor of prolyl and lysyl hydroxylase, which are enzymes essential for the stabilizing and cross-linking of newly formed collagen molecules. In humans, the use of a 5% Vitamin C cream resulted in a significantly improved skin relief and a decrease in deep furrows after a six month period of use as compared to placebo. (See Humbert et al., Exp Dermatol 12:237-44 (2003)).

Polyphenols

Those skilled in the art will recognize that polyphenols are usually composed of two or more aromatic rings, each containing at least one hydroxyl group, and their antioxidant properties arise from their high reactivity as hydrogen or electron donors, from the ability of the polyphenol-derived radical to stabilize the unpaired electron, and from their ability to chelate transition metal ions such as Fe(II). (See Dreher et al., "Antioxidants", Chapter 13 in Textbook of Cosmetic Dermatology, at page 118, 2$^{nd}$ col.). Moreover, polyphenols are also thought to be able to quench singlet oxygen, superoxide anion radicals, and peroxyl radicals. (See id.).

By way of non-limiting example, the one or more polyphenols used in the antioxidant compositions of the invention may be selected from flavonoids; flavonols; flavones; catechins; flavanones; anthocyanidins; isoflavonoids; and/or extracts from green tree (e.g., epigallocatechin gallate (EGCG), milk thistle, soybeans, wine grapes and their seeds, acai berry, coffee berry, feverfew, pomegranate, tropical ferns, and turmeric. (See id.).

In recent years, extracts from dietary and medical plants have gained considerable attention as efficient agents protecting skin from UVR-induced photodamage after topical application. (See Afaq et al., Skin Pharmacol Appl Skin Physiol 15:297-306 (2002); Berson, J Drugs Dermatol 7(7 Suppl):s7-12 (2008); Baumann et al., J Drugs Dermatol 8(6 Suppl):s5-9 (2009); Ditre et al., Cutis 82 (6 Suppl):2-16 (2008)). Extracts from green tea, milk thistle, soybeans, wine grapes and their seeds, as well as from açai berry, coffee berry, feverfew, pomegranate, tropical ferns, and turmeric were particularly studied. They contain a wide variety of polyphenols known as flavonoids.

Polyphenols usually are composed of two or more aromatic rings, each containing at least one hydroxyl group. Flavonoids are divided into flavonols, flavones, catechins, flavanones, anthocyanidins and isoflavonoids, depending on their chemical structure. They are synthesized conjointly with ascorbic acid, Vitamin E, GSH and numerous other antioxidant enzymes by plants as a response to mitigate cellular damage under oxidative conditions.

The antioxidant properties of polyphenols arise from their high reactivity as hydrogen or electron donors, from the ability of the polyphenol-derived radical to stabilize the unpaired electron, as well as from their ability to chelate transition metal ions such as Fe(II) and thereby interfering with the hydroxyl radical production. Besides hydroxyl radicals, polyphenols are believed to quench singlet oxygen, superoxide anion radicals and peroxyl radicals. Moreover, polyphenolic compounds possess also anti-inflammatory and other properties beneficial for skin.

Green Tea Polyphenols

Green tea (Camellia sinensis) extracts are possibly the most extensively studied plant derived antioxidants for skin. (See Hsu, J Am Acad Dermatol 52:1049-59 (2005)). In contrast to black tea, which is fermented, green tea leaves contain high concentrations of polyphenols, including epigallocatechin-gallate (EGCG). Green tea polyphenols act as antioxidants by scavenging ROS and reactive nitrogen species as well as by sequestering metal ions. They act indirectly as antioxidants through inhibition of "pro-oxidant" enzymes such as inducible nitric oxide synthase, lipoxygenases and cycloxygenases and induction of antioxidant enzymes GSH-S-transferases and SOD. (See Frei et al., J Nutr 133:3275 S-84S (2003)).

The protective effects of green tea extracts and their major polyphenolic constituent, EGCG, on UVR-induced skin damage after topical application were first observed in several animals models. (See Hsu, J Am Acad Dermatol 52:1049-59 (2005)). Later, these effects were confirmed in human studies, where topical application of green tea extracts or EGCG significantly decreased erythema responses, lipid peroxidation as well as DNA-damage. (See Katiyar et al. Carcinogenesis 22:287-94 (2001); Elmets et al., J Am Acad Dermatol 44:425-32 (2001)). More recently, a placebo controlled study with 40 women with moderate photoaging demonstrated that the combined use of a 10% green tea cream and oral green tea supplementation (300 mg) twice daily for eight weeks resulted in a significant improvement in elastic tissue. (See Chiu et al., Dermatol Surg 3:855-60 (2005)). However, a trend toward improvement (but no significant differences in clinical grading) was found between green tea treated group and placebo, indicating that a longer treatment period may be required for clinically relevant improvements.

In another placebo-controlled study, topical application of a green tea protected human skin from solar-simulated ultraviolet light when applied 15 minutes prior to exposure and reapplied immediately after exposure to two minimum erythema doses. (See Camouse et al., Exp Dermatol 18:522-26 (2009)). This study did not reveal any difference between green and white tea extracts. A further study showed that three-time daily use of a lotion containing 0.4% of a green tea extract with 40-50% total polyphenol content helped to reduce UVB-mediated increase in sunburn cell formation (apoptotic keratinocytes) and p53 expression in keratinocytes but did not reduce erythema or formation of thymidine dimmers. (See Mnich et al., Exp Dermatol 18:69-77 (2009)).

Thus, this study clearly indicates that skincare formulation with relative low concentrations of green tea extracts (i.e., providing about 0.2% total polyphenols), which makes them more cosmetically acceptable, are efficient for photoprotection.

Green tea extracts and EGCG were further demonstrated to have chemopreventive effects in rodents and therefore prevent cancer. However, epidemiologic and human studies have not yet been conclusive, which may be the result of multiple factors including different bioavailabilities between humans and rodents. (See Hsu, J Am Acad Dermatol 52:1049-59 (2005)); Boehm et al., Cochrane Database Syst Re 8(3):C2005004 (2009)).

Other Polyphenols

Topical application of silymarin in mice, a milk thistle extract containing silibinin as predominant polyphenol, was shown to inhibit UVB-induced immunosuppression, to reduce UVB-induced sunburn cell formation, to prevent DNA adduct formation as well as to prevent photocarcinogenesis. (See Singh et al., Antioxid Redox Signal4:655-63 (2002); Saller et al., Forsch Komplementmed 14:70-80 (2007)).

Genistein is a major flavonoid constituent of soybean. While much of the reports on genistein have focused on its role as phytoestrogen and tyrosine kinase inhibitor, it also has antioxidant properties. Topical administration of genistein substantially inhibited UVR-induced hydrogen peroxide formation, lipid peroxidation and DNA-damage in mice and protects human skin against UVB-induced erythema. (See Wei et al., J Nutr 133:3811 S-3819S (2003)).

Another human study evaluating phenolic plant extracts revealed that topical application of a tropical fern extract reduced erythema as well as UVA-induced immediate pigment darkening and delayed tanning when applied before UVR exposure. (See Gonzalez et al., Photodermatol Photoimmunol Photomed 13:50-60 (1997)).

Coffee berry, the unripe coffee bean, contains diverse (poly)phenolic compounds including chlorogenic acid, quinic acid, ferulic acid and condensed proanthocyanidins. In a clinical study, a skincare system with 1% coffee berry extract resulted in a significant improvement in signs of skin aging when compared to vehicle. (See Farris et al., Dermatol Ther 20:322-29 (2007)).

Pomegranate fruit extract, which contains the polyphenol ellagic acid, possesses strong antioxidant and anti-inflammatory properties and limited UVB-mediated damage in a human reconstituted skin model. (See Afaq et al., Exp Dermatol 18:553-61 (2009)).

Another natural extract, a parthenolide-depleted extract of feverfew, which was free of sensitization potential, has free radical scavenging activity against a wide range of ROS. In a clinical study topical feverfew treatment significantly reduced erythema versus placebo 24 h after UV exposure. (See Martin et al., Arch Dermatol Res 300:69-80 (2008)).

Additional studies are warranted in order to help clarify whether the observed beneficial effects of the botanical extracts or their constituents might be partially attributed to their sunscreening properties under the respective study conditions (e.g., UVR-source, concentration and dose of extract applied per surface area), in particular in the UVA range.

Thiol Antioxidants

Thiol antioxidants, such as GSH, N-acetylcysteine, lipoic acid and their derivatives are another important group of potent radical scavengers. (See Thiele et al., Antioxidant defense systems in skin, In Elsner et al., eds, Cosmeceuticals—Drugs vs. Cosmetics (Dekker: New York, 2000) 145-

87; Thiele et al., Oxidants and Antioxidants in Cutaneous Biology, In Burg, ed. Current Problem in Dermatology 29 (Karger: Basel 2001)). Topical administration of GSH, GSH-ethyl ester and N-acetylcysteine, respectively, efficiently protected against UVB-radiation induced epidermal lipid peroxidation, cytotoxicity and apoptosis using pig skin ex vivo as skin model for assessing short-term biochemical effects related to UVB. (See Rijnkels et al., Radiat Res 159: 210-17 (2003)). Their photoprotective effects have been reported in few clinical studies. Topical treatment with N-acetylcysteine under occlusion resulted in an increased GSH level and eliminated its oxidized form (GSSG) in human skin in vivo. (See Kang et al., J Invest Dermatol 120:835-41 (2003)). Thus, in addition to its direct antioxidant properties, stimulation of GSH-biosynthesis might be a key mechanism accounting for the observed photoprotective effects of N-acetylcysteine.

In addition, dihydrolipoic acid, the reduced and primarily active antioxidant form of alpha-lipoic acid, seems a promising thiol-antioxidant potentially protecting against oxidative stress when applied onto skin. Dihydrolipoic acid is known to scavenge singlet oxygen, superoxide anion radicals, hydroxyl radicals and peroxyl radicals. (See Thiele et al., Oxidants and Antioxidants in Cutaneous Biology, In Burg, ed. Current Problem in Dermatology 29 (Karger: Basel 2001)). A placebo-controlled, split-face study with 33 women indicated that several clinical characteristics related to photoaging of facial skin improved after application for 12 weeks of a 5% lipoic acid cream. (See Beitner, Br J Dermatol 149:841-49 (2003)).

"Other" Antioxidants

The pineal hormone melatonin (N-acetyl-5-methoxytryptamine) is also an antioxidant and has been shown to significantly reduce UVR-induced erythema in humans. (See Dreher et al., Br J Dermatol 139:332-39 (1998)). Apart from melatonin's antioxidant properties, its dose-dependent sunscreening properties, as well as its supposed immunomodulatory function might have contributed to the observed photoprotective effects.

In addition, L-ergothioneine which is a thiourea derivative of histidine found in food plants and mushrooms seems another promising potent antioxidant as judged from in vitro studies. (See Dong et al., J Cosmet Dermatol 4:167-73 (2007). Idebenone, a synthetic analogue of coenzyme Q which is presumed to penetrate skin more efficiently than its parent compound is another potent antioxidant as shown in vitro. (See McDaniel et al, J Cosmet Dermatol 4:10-17 (2005)). A clinical study with a 1% idebenone formulation demonstrated a reduction in fine lines/wrinkles in female subjects between 30 to 65 years of age with moderate photodamage. (See McDaniel et al., J Comet Dermatol 4:167-73 (2005)). However, this study was not vehicle controlled. Furthermore, a study in pigs revealed that idebenone offers little to no photoprotective effects when applied daily for four days before irradiation with solar simulated UV radiation up to five minimal erythema doses. (See Tournas et al., J Invest Dermatol 126:1185-87 (2006)).

Antioxidant Combinations

As illustrated, when discussing the cutaneous antioxidant system, antioxidants interact when combined. Emanating radical or oxidized forms of antioxidants after ROS scavenging may be quickly regenerated in the presence of appropriate co-antioxidants. Accordingly, an enhanced (i.e., synergistic) photoprotective effect may be obtained by applying distinct combinations of antioxidants. For instance, ample evidence exists about the interactive dependence of Vitamins C and E in diminishing photodamage in vivo.

A single topical application of a combination of 2% Vitamin E and 5% Vitamin C in humans resulted in more pronounced photoprotective effect as compared to the application of either antioxidant alone in the identical vehicle. (See Dreher et al., Br J Dermatol 139:332-39 (1998)). Moreover, the same study demonstrated that the most dramatic improvement resulted from the co-formulation of melatonin together with α-tocopherol and ascorbic acid. Possible synergistic interactions between melatonin and the Vitamins E and C could have contributed to the observed, significantly increased photoprotective effects.

Other distinct mixtures of topically applied antioxidants were also shown to be more effective in reducing photodamage than single antioxidants. For example, adding 0.5% ferulic acid (a phenolic antioxidant found in plants) to a solution of 1% α-tocopherol and 15% ascorbic acid doubled photoprotection to solar simulated irradiation of pig skin when applied topically from 4- to 8-fold as measured by both erythema and sunburn cell formation. (See Lin et al, J Invest Dermatol 125:826-32 (2005)).

Another combination consisting of ferulic acid with tocopheryl acetate and alpha-glycosylrutin was shown to limit the severity of experimentally induced polymorphous light eruptions when applied one week prior to photoprovocation with UVA in humans. (See Hadshiew et al., Dermatology 195:362-68 (1997)). Recently, remarkably enhanced antioxidative efficacy as compared to additive efficacy was found for the mixture green tea polyphenols, α-tocopherol and ascorbic acid. (See Dai et al., Biochemie 90:1499-505 (2008). Kinetic and mechanistic studies revealed that the antioxidant synergism was due to the regeneration of α-tocopherol by the green tea polyphenols, while latter are regenerated by ascorbic acid.

Therefore, the antioxidant synergism between green tea polyphenols, ascorbic acid and α-tocopherol makes this combination of antioxidants particularly interesting for antioxidant protection.

However, it is not obvious to formulate combinations of antioxidants in a composition which remains stable over a period of months to years (as illustrated in Example 3, infra); provides a high antioxidant power and, at the same time, a very fast reaction time (as illustrated in Example 3, infra); penetrates into skin within few minutes and increases the antioxidant power of skin (as illustrated in Example 4, infra); targets mitochondrial oxidative stress (i.e., through the presence of creatine); and is also suitable for topical application. In addition, it is not obvious to formulate combinations of antioxidants in a composition which do not lead to pro-oxidative effects after topical application onto skin (i.e., decreases the antioxidant capacity of skin), both without exposure to solar UVR (as illustrated in Example 4, infra) and in combination with exposure to solar UVR (as illustrated in Example 5, infra). Furthermore, it is also not obvious from the teachings of the prior art to prepare a stable composition suitable for topical application, which also provides higher antioxidant power and faster reaction time than the compositions known in the art (as illustrated in Example 3, infra). The compositions of this invention provide, for the first time, all of these attributes and fulfills a long-felt need in the art for such compositions.

Importantly, in order to determine the power and reaction time for antioxidants or antioxidant combinations correctly, adequate antioxidant measuring methods, including, for example, electronic spin resonance (ESR), must be used. ORAC and other decolorization antioxidant assays do not provide an adequate measure for antioxidant power and reaction time. Because non-ESR methods do not provide accurate antioxidant measurements and, therefore, relevant in vitro and ex vivo data for antioxidants and/or antioxidant combinations, such data is not relevant to the antioxidant compositions of the instant invention.

Topical Application of Antioxidants

Topical administration of antioxidants can be used to increase antioxidant tissue levels in human epidermis and dermis. Non-limiting examples of such antioxidants can include (but are not limited to) Vitamin E (e.g., α-tocopherol), Vitamin C (e.g., ascorbic acid), polyphenols (e.g., flavonoids, flavonols, flavones, catechins, flavanones, anthocyanidins, and/or isoflavonoids), thiol antioxidants (e.g., GSH, N-acetylcysteine, and lipoic acid), melatonin, L-ergothioneine, idebenone, and the like. (See Dreher et al., "Antioxidants", Chapter 13 in Textbook of Cosmetic Dermatology, at pages 118-120).

Animal and human studies have convincingly demonstrated that topical application of antioxidants helps protect skin from UV-induced damages. The protective effects in humans were particularly well studied for ascorbic acid, tocopherol, some of their ester derivatives, as well as polyphenolic antioxidant mixtures including green tea extracts. Importantly, their efficacy was significantly increased when applied as combination. In fact, the combination of ascorbic acid, tocopherol and ferulic acid or, respectively, green tea, appear synergistic antioxidant combinations. Accordingly, regular application of skincare products containing combinations of antioxidants efficiently protect skin against exogenous oxidative stressors occurring during daily life. Because sunlight induced skin damage is not solely dependent on occurrence of oxidative stress, antioxidant supplementation cannot be presumed to give complete photoprotection. In fact, photoprotective effects of most antioxidants are modest as compared to sunscreens (J Am Acad Dermatol 2011 65(3): 525-530, which is incorporated herein by reference). Therefore, improved antioxidant compositions are needed. Hence, as of today, sunscreens remain indispensable to effectively prevent skin photodamage.

Sunscreens do benefit from combination with antioxidants resulting in increased efficacy of such photoprotective products. This was first recognized by Darr and coworkers who were able to demonstrate that a combination of Vitamins C and E with oxybenzone resulted in an apparently greater than additive protection against phototoxic damage in pigs. (See Darr et al., Acta Derm Venereol 76:264-68 (1996)). This observation was later confirmed by others in humans. (See Dreher et al., Br J. Dermatol 139:332-39 (2007); Matsui et al., J Investig Dermatol Symp Proc 14:56-59 (2009)). Therefore, any of the antioxidant compositions are preferably combined with one or more sunscreen actives (e.g., oxybenzone, octinoxate, zinc oxide, titanium dioxide, etc.) in order to provide products with increased photoprotective benefits.

Antioxidants are mostly of protective nature (i.e., protective from oxidative stress) and, with the exclusion of L-ascorbic acid, they generally have no effect in reversing skin wrinkles or folds. In fact, only agents which promote collagen formation including retinoic acid or human growth factors such as basic fibroblast growth factor or transforming growth factors beta may reverse signs of skin aging. (See Rangarajan et al., Topical growth factors for skin rejuvenation, In: Textbook of Skin Aging, Farage et al, eds. (Springer, 2010), pages 1097ff). However, few antioxidants have effects beyond their "pure" ROS and RNS scavenging activity that are relevant to extracellular matrix metabolism. For example, as shown in artificial skin, EGCG, the major polyphenol in green tea extract, decreased the level of matrix metalloproteinase (MMP) production and increased their tissue inhibitor (TIMP) expression level similarly as retinoic acid. (See Lee et al., J Dermatol Sci 40:195-204 (2005)).

Table 2 shows the antioxidants and concentration ranges that can be included in antioxidant compositions according to the instant invention:

TABLE 2

| | |
|---|---|
| Ascorbic Acid | 1 to 30% |
| Tocopherol | 0.1 to 5% |
| Dimethylmethoxy chromanol | 0.01 to 1% |
| Epigallocatechin Gallate (EGCG) | 0.01 to 0.5% |
| Creatine | 0.1 to 5% |

In one preferred embodiment, the antioxidant composition of the invention includes all of these antioxidant components (in the concentration ranges shown in Table 2). Any other combinations of the antioxidants in Table 2 can also be used. For example: ascorbic acid, tocopherol, and EGCG; ascorbic acid, tocopherol, EGCG, dimethylmethoxy chromanol; ascorbic acid, tocopherol, EGCG, and creatine; etc. Determination of other suitable antioxidant components and/or concentration ranges that can be used in accordance with the instant invention is within the routine level of skill in the art. Likewise, determination of additional (and/or alternative) antioxidants to be used in the compositions of the invention is also within the routine level of skill in the art. In one preferred embodiment, ascorbic acid is in its L-form. Preferably, the ascorbic acid is micronized.

Comparing Antioxidant Potency

Following the creation of oxidative stress, antioxidant efficacy can be measured by differing methods. For example, the response can be measured using decolorization assays (e.g., oxygen radical absorbance capacity (ORAC)), using electron spin resonance (ESR), measuring erythema, and/or measuring biological endpoints of oxidative stress (e.g., oxidation of skin biomolecules, including, but not limited to DNA, lipids, polysaccharides, and/or proteins). Those skilled in the art will recognized that examples of the oxidation of skin biomolecules can include formation of 8-OHdg (8-hydroxydeoxyguanosine), lipid peroxidation (through malondialdehyde), AGEs (advanced glycation end-products), etc.

Those skilled in the art will recognize that there are other antioxidant assays that are commonly used to determine the activity level of antioxidant ingredients. These include, for example, oxygen radical absorbance capacity (ORAC), which is an in vitro assay developed to assess the total antioxidant capacity of a given sample; Trolox®-equivalent antioxidant capacity (TEAC), which measures inhibition of free radical cation by the antioxidant sample relative to the antioxidant Trolox®; and Oxidative Stability Index (OSI), which is a method designed to measure oxidative stability. (See Chen et al., Photodermatology, Photoimmunology & Photomedicine 28:228-34 (2012), at pages 228-231).

ORAC measures free radicals indirectly through the use of a fluorescent dye. In this method, ROS generators (e.g., AAPH (2,2'-azobis(2-amidino-propane)dihydrochloride)) are added to parallel reactions containing equivalent amounts of fluorescent probe. Reactions contain either an antioxidant or buffer blank. Loss of fluorescence due to oxidative damage to the probe is then measured kinetically. The AUC is calculated as the integral of the area under the curve. The resultant antioxidant capacity is the difference between the AUC of the sample and that of the buffer blank.

However, ORAC may not be the most accurate method to measure antioxidant efficacy, as this method does not evaluate the characteristics of the antioxidants and does not necessarily show the capacity to suppress oxidation (i.e., antioxidation). (See Niki, Free Radical Biology and Medicine 49:503-15 (2010)).

In contrast, ESR is the only assay method that directly quantifies free radicals without the need for scavenging techniques. (See Chen et al. at pages 231-232). Thus, ESR is a more accurate method to determine the antioxidative power of an antioxidant composition because it allows the direct measurement of free radicals.

The efficacy of antioxidants is measured by the Antioxidative Power (AP), which is qualified by its capacity and qualified by its reaction time.

The AP of an antioxidant composition can be measured using the ESR technology based on the measure described in Herrling et al., Int. J. Cosm Sci. 1-6 (2012).

Those skilled in the art will recognize that the reaction of certain nitroxides as a probe for free radical detection with the generated free radicals species results in the loss of their ESR signal. (See Herrling et al., at page 1, $1^{st}$ col.). Thus, certain nitroxides can be used as a probe for free radical detection in vitro, ex vivo and also in vivo, and the effect of pharmaceutical and/or cosmetic skin products on skin's antioxidant status can be quantified ex vivo (and in vivo) in accordance with the method described in Herrling et al.

Surprisingly and unexpectedly, the antioxidant composition described in Table 2 has a very high AP value and also a fast, short reaction time that had not previously been observed with other antioxidants and/or antioxidant combinations.

Antioxidant Compositions of the Invention

The antioxidant compositions of the instant invention all possess a variety of important properties, characteristics, and/or advantages as compared to other antioxidant compositions known in the art. For example, these can include, but are not limited to:

Limiting external/environmental and internal/mitochondrial oxidative stress.
Replenishing the skin's antioxidant network and providing synergistic antioxidant effects.
Allowing the use of high to maximal concentration range of Vitamin C (up to 30%).
Stimulating the skin's natural thiol antioxidant cycle through EGCG.
Reducing mitochondrial oxidative stress trough Creatine.
Allowing the use of micronized Vitamin C particles, which helps to increase stability of the Vitamin C in the compositions.
Allowing the use of excipients that are predominantly (e.g., greater than 50%) silicone oils.
Being substantially free of water (e.g., less than 1%).
Being free (e.g., less than 0.1%) or containing less than 10% glycols (e.g., propylene glycol, butylene glycol, etc.) or poly-glycols (PEGs, PPGs, etc.).
Providing stable formulations. Those skilled in the art will recognize antioxidantcompositions in accordance with the instant invention are more stable than other high concentration (e.g., more than 10%) Vitamin C formulations known in the art.
Possessing elegant cosmetic attributes as compared to other high concentration (e.g., more than 10%) Vitamin C formulations. Those skilled in the art will recognize that the antioxidant compositions of the instant invention are easy to apply (e.g., since composition can be formulated as semi-solid formulations).
Having higher antioxidant power than other antioxidant formulations.
Possessing faster reaction time for neutralization of free radicals than other antioxidant formulations.
Being able to be made free of preservatives such as parabens.
Increasing the skin's antioxidant power within a very short period of time (e.g., after 5 minutes) following topical application.

One example of an antioxidant composition according to the invention, marketed as RéActive Antioxidant Serum (Neocutis Inc., San Francisco, Calif.), contains 15% L-ascorbic acid, 1% alpha-tocopherol, 0.1% epigallocatechin gallate (EGCG), 0.05% dimethylmethoxy chromanol, and 0.5% creatine. Like all of the compositions of the present invention, the RéActive composition contains antioxidants to help replenish the skin's antioxidant network; provides synergistic antioxidant effects; contains creatine, which addresses mitochondrial oxidative stress; is a stable silicone-based formulation that uses micronized Vitamin C (ascorbic acid) particles; possesses elegant cosmetic attributes, is easy to apply, and is free of preservatives. A comparison of the antioxidative power as measured by ESR of RéActive Antioxidant Serum (corresponding to Product A, an example of a composition according to this invention) with four other marketed antioxidant products (corresponding to Products B, C, D, and E, which are not examples of compositions according to this invention) is shown in FIGS. 1A-1B.

Any of the antioxidant compositions described according to the invention may contain one or more additional ingredients, including one or more additional substances (e.g., acceptable carriers and/or excipients) suitable for topical application can also preferably be used in these compositions. The one or more additional ingredients may also include additional substances with biological activities (i.e., biologically active agents).

In any of the method described herein, skin or skin cells (e.g., epidermal keratinocytes, dermal fibroblasts) are contacted (i.e., topically, subcutaneously, or by any other suitable method known in the art) with the antioxidant compositions. Additionally, the methods may also involve contacting (i.e., topically, subcutaneously, or by any other suitable method known in the art) mucosa (i.e., mucous membranes) or mucosal cells (i.e., epithelial cells) with the antioxidant compositions.

The compositions can be an aerosol, emulsion, liquid, lotion, cream, paste, ointment, serum, foam, spray, patch, microneedle device or any other cosmetic, dermatological and pharmaceutically acceptable formulation or device. Generally, an acceptable formulation for cosmetic, dermatological, and/or pharmaceutically use would include any acceptable carrier, excipient, and/or substance suitable for use on human skin or mucosa. The compositions may also contain one or more other biologically active agents including, but not limited to, retinoids, growth factors, and/or peptides.

Any of the compositions of the present invention may also be used in combination with other cosmetic, skin care, feminine, hygiene, dermatological, pharmaceutical products, and/or medical devices.

The compositions of the invention can be used in humans. Alternatively, the composition may also be used in any kind of animal, preferably in mammals, and more preferably in cows, horses, cats, dogs, pigs, goats, or sheep.

Demonstrating Clinical Efficacy

Prevention, amelioration, and/or treating of the signs of free radical related skin damage (due to acute and/or chronic exposure to source(s) of free radicals) are functional features which can be visualized, analyzed, measured and quantified using many techniques known by the specialist in cosmetic or skin rejuvenation treatments. Decrease of fine lines, wrinkles, skin folds, and of skin roughness can be quantified either directly on the person contact-free using fringe projection (FOITS=Fast Optical In vivo Topometry System; Dermatop™ or Primos™ system), or by silicon replicas of the skin area which are then analyzed by the technique called "drop shadows" or by a FOITS system, or by a Canfield VISIA™ device. Changes in volume and shape of the face can be quantified using a relief obtaining system without contact using a fringe projection FOITS system. Alteration of the skin barrier can be quantified by measuring transepidermal water loss (TEWL) using a Tewameter™, a Vapometer™, a Dermalab™ and/or an Aquaflux™ device. Loss of firmness and/or elasticity and/or tone and fatigue of the skin can be quantified using a Cutometer™, a Reviscometer™, an Aeroflexmeter™, a Dynaskin™, a Ballistometer™, a Twistometer™ and/or a Dermalab™ device. Dull complexion, loss of uniformity of skin tone, pigmentation changes (hypo and hyper pigmentation), local reddening, loss of clarity and brightness of the complexion, pigmentation spots, rosacea, dark circles are directly measurable using a Mexameter™, a Chromameter™, a Colormeter™, a Canfield VISIA™, a Canfield VISIA-CR™, a SIAscope™, a Goniolux™ or a confocal laser microscope device, and/or by specific color analysis on photo (enabled by the technique of photographing in polarized crossed and parallel light). The number and size of facial pores can be quantified by the silicon replica technology described above, or by specific analysis on photo (enabled by using a video microscope or a macroscopic photographing system). Atrophy and thinning of the skin, epidermis, dermis, or hypodermis (e.g., in case of studying slimming agents) is measurable by measuring TEWL (e.g., in case of studying the epidermis), or by an ultrasound echographic device, and/or a confocal laser microscope device. Density of skin fibers can be quantified by ultrasound and then by image analysis. Cellulite is quantified either directly by a relief obtaining system without contact using fringe projection (FOITS) or indirectly by measuring the length of the dermo-hypodermal junction by an ultrasound echographic device. Stretch marks are either directly quantified using a relief obtaining system without contact using fringe projection (FOITS) or by the silicon replica technology. Skin softness is directly measurable by techniques of friction study as with a frictiometer device or indirectly by the silicon replica technology. Changes in collagen, extracellular matrix components, and/or in connective tissue fibers may be quantified by histology, confocal laser microscopy, UV spectroscopy, SIAscopie, and/or by multiphoton spectroscopy. All changes visible to the eye (including but not limited to fine lines, wrinkles, folds, texture, sagging, loss of elasticity color, tone, pigmentation, redness) can be quantified in direct or on photography, by a trained judge person or not, with or without visual scoring system (e.g., using a 4-point severity scale).

Cosmetic Product and Medicament

The terms "cosmetic composition" and "cosmetic product" are used interchangeably herein relate formulations that can be used for cosmetic purposes or purposes of hygiene or as a basis for delivery of one or more cosmetic and/or pharmaceutical substances, products, and/or ingredients.

The terms "pharmaceutical composition" and "medicament" is used herein to refer to a formulation that can be used for medical purposes or as a basis for delivery of one or more cosmetic and/or pharmaceutical substances, products, and/or ingredients.

It is possible that any of the formulations, compositions, medicaments, and/or products described herein can be used for two or more of these same purposes at one time.

Preferably, the compositions described herein are suitable for "topical application" (i.e., on top of skin surface, on top of mucosal surface). As used herein, topical application includes, but is not limited to, cutaneous; ocular; mucosal; buccal; vaginal; vulvar administration; administration onto skin, scar, keloid, scalp, eye, mouth, nose, vulva, vagina, rectum; and/or administration into a wound, ulcer, and granulation tissue.

Alternatively, the compositions may be suitable for subcutaneous administration.

Cosmetic Product

A "cosmetic product," as used herein, include without limitation, personal care product, skin product, skin cream, skin gel, skin ointment, skin lotion, skin serum, anti-aging product, skin rejuvenation product, skin conditioner, moisturizer, feminine product, hygiene product, skin patch, skin mask, tissue wipe, lipstick, mascara, rouge, foundation, blush, eyeliner, lip liner, lip gloss, lip balm, facial or body powder, sunscreens, sunblocks, nail polish, mousse, sprays, styling gels, nail conditioner, bath and shower gels, shampoos, conditioners, cream rinses, hair sprays, hair dyes and coloring products, soaps, body scrubs, exfoliants, astringents, depilatories and permanent waving solutions, anti-dandruff formulations, anti-sweat and antiperspirant compositions, shaving, preshaving and after shaving products, leave-on conditioners, deodorants, cold creams, deodorants, cleansers, rinses, vulvar product, vaginal product, or the like; whether in the form of creams, lotions, gels, ointments, macro-emulsions, micro-emulsions, nano-emulsions, serums, balms, colloids, solutions, liquids, suspensions, dispersions, compacts, solids, powders, pencils, spray-on formulations, brush-on formulations, patches, iontophoretic patches, microprojection patches, microneedle patches, skin delivery enhancing systems, bandage, tissue cloths, wipes, masks, aerosols, pastes, soap bars, cosmetic devices, and/or any other forms readily known to those skilled in the art.

Medicament

A "medicament" as used herein, include without limitation pharmaceutical preparations, carriers for dermatological purposes, including topical and transdermal application of pharmaceutical ingredients. These can be in the form of creams, lotions, gels, ointments, macro-emulsions, micro-emulsions, nano-emulsions, serums, balms, colloids, solutions, liquids, suspensions, dispersions, compacts, solids, powders, pencils, spray-on formulations, brush-on formulations, patches, iontophoretic patches, microprojection patches, microneedle patches, skin delivery enhancing systems, bandages, tissue cloths, wipes, masks, aerosols, pastes, soap bars, medical devices, and/or any other forms readily known to those skilled in the art.

Suitability for Topical Application

The term "acceptable substance(s) for topical application" and the like, as used herein, mean that the composition(s) comprising "acceptable substance(s) for topical application" according to the invention are suitable for use in contact with human skin and/or human mucosa; where the skin or the mucosa can be healthy, newborn, young, old, aged, appear visually different than normal, damaged, photo-damaged, sunburned, wrinkled, pathologic, diseased, wounded, atrophic, irritated, compromised, treated with cosmetic product(s), treated with pharmaceutical product(s), treated with cosmetic procedure(s), treated with dermatological procedure(s), treated with a pharmaceutical or medical device(s), surgically treated, etc. and are absent of allergy to skin or mucosa, and are also absent of significant (consumer-unacceptable, corresponding to more than mild) irritation to skin or mucosa, and the like after repeated topical application for cosmetic, skin care, feminine, or similar uses.

Irritation and allergy to skin (also called contact dermatitis and allergy) in humans can be determined by acute (1 day) and repetitive (4 to 21 days) patch testing on the back of humans, and/or during in use tests where the composition is used as indicated (e.g., for topical use on face, vulva, vagina, mucosal surface, and/or other body surface areas; or for wound healing). In case of a medication, safety studies generally also include animal studies.

Furthermore, acceptable substance(s) for topical application means that the compositions comprising "acceptable substance(s) for topical application" in accordance with the present invention are without significant physicochemical instability (e.g., viscosity, pH, specific gravity) in the final packaging (e.g., bottle, tube, pump, jar, airless container, spray, patch, etc.) during the shelf-life of the product according to the recommended storage conditions of the product. Significant physicochemical instability means, that the viscosity, pH, or the specific gravity changed (increased, decreased) more than 10% from the time when the composition was prepared and filled into the final packaging.

Any of the compositions of the present invention may also provide good aesthetics and be cosmetically elegant.

Acceptable substances for topical application or administration may include suitable excipients and/or carriers known in the art.

Additional Substances

The antioxidant compositions described herein preferably include at least one topically acceptable silicone oil and/or non-silicone oil in combination with Vitamin C, Vitamin E and one or more polyphenol antioxidants. Optionally these compositions are in combination with at least one additional substance suitable for topical application and/or subcutaneous application. Additional substance(s) can be inert (e.g., carriers and/or excipients) or can be with biological activities (i.e., biologically active agents and/or active pharmaceutical ingredient). Preferably, the compositions of the invention may also include additional biological active agents.

The terms "substance", "ingredient", "agent" and the like are used interchangeably herein.

The compositions of the invention may include one or more substances, various, conventional or not, which will provide some benefit to the object of the composition.

The choice of additional substances to be included in the composition is made depending on the constraints relating to the components of the antioxidant compositions described herein (e.g., stability, solubilization, etc.), if enhanced and/or additional benefits and properties (e.g., anti-acne, anti-microbial, anti-wrinkle, skin lightening, anti-redness, additional antioxidant, skin protectant, sunscreen, hair growth, anti-inflammatory, emollient, moisturization, enhanced skin penetration, etc.) of the composition are desired, and, where applicable, the use subsequently envisaged for the composition.

The compositions of the invention may include one or more additional substances, various, conventional or not, which will provide some benefit to the object of the composition.

Of course, a decision to include an additional ingredient or substance and the choice of a specific ingredient or substance depends on the specific use of the composition and the product formulation.

In particular examples, the compositions of the present invention may contain a wide range of additional ingredients. The 2012 International Cosmetic Ingredient Dictionary & Handbook, 14th Edition, as well as the Cosmetic Bench Reference—Directory of Cosmetic Ingredients (published by Cosmetics & Toiletries) describes a wide variety of non-limiting cosmetic and pharmaceutical ingredients commonly used in the skin care, personal care, feminine care, and dermatology and pharmaceutical industry, which are available for use in the present invention. Additional examples can be found in the books provided by the United States Pharmacopeia (USP), the National Formulary (NF), and other references for cosmetic and pharmaceutical ingredients known in the art. Each of these references is herein incorporated by reference in its entirety. This information is regularly updated by the addition of new ingredients.

Exemplary functional classes of such ingredients are, but are not limited to, abrasive agent, absorbent powder, absorption base, acidulent, activator, adhesion promoter, agent modulating cell differentiation, agent modulating cell proliferation, agent stimulating synthesis of dermal or epidermal macromolecules, agent preventing degradation of dermal or epidermal macromolecules, agent acting on microcirculation, agent acting on skin barrier, agent acting on energy metabolism of cells, agent increasing the substantivity, antimicrobial sequestering agent, analgesic agent, anesthetic agent, antacid agent, anti-acne agent, anti-aging agent, anti-wrinkle agent, anti-atrophy agent, anti-androgen agent, anti-bacterial agent, anti-scar agent, anti-seborrheic agent, anti-cracking agent, anti-cellulite agent, anti-stretch mark agent anti-dandruff agent, anti-foam agent, anti-fungal agent, anti-histamine agent, anti-inflammatory agent, anti-irritant agent, anti-microbial agent, anti-mite agents, antibiotic agent, antiviral agent, antioxidant agent, anti-glycation agent, anti-neoplastic agent, anti-cancer agent, anti-skin cancer agent, anti-eczema agent, anti-psoriasis agent, anti-pollution agent, antiperspirant agent, anti-pruriginous agent, anti-pruritic agent, antiseptic agent, antistat agent, astringent, α-adrenergic receptor agonist, barrier agent, binding agent, bio-adhesive agents, botanical agent, botanical extract, biological additive, buffer agent, bulking agent, calcium sequestering agent, calming agent, carrier agent, chemical additive, cell lysate, cell culture medium, conditioned cell culture medium, chelating agent, circulatory stimulant agent, cleansing agent, collagen stimulating agent, co-emulsifier agent, colorant, conditioning agent, controlled release agent, cooling agent, co-solvent, coupling agent, curative agent, denaturant, deodorant agent, depilatory agent, desquamating agent, detangler agent, detergent, disinfectant, dispersant, dye stabilizer, dermatologically acceptable carrier, elastin stimulating agent, extracellular matrix stimulating agent, emollient, emulsifier, emulsion stabilizer, enzyme, enzymatic inhibitor, enzyme-inducing agent, coenzyme, cofactor, essential oil, exfoliant, fat soluble agent, fiber, film former, fixative, flavor, foam booster, foam stabilizer, foaming agent, fragrance, free radicals scavenger, fungicide, gellant, glosser, hair beaching agent, hair growth promoter, hair colorant, hair conditioning agent, hair-set polymer, hormone, hormone-like agent, humectant, hydrophobic agent, hydrotropic agents intermediate agent, hyaluronic acid stimulating agent, keratolytic agent, lathering agent, lipolytic agent, lubricant, make-up agent, moisture barrier agent, moisturizer, muco-adhesive agents, muscle relaxant, natural moisturizing factor, neutralizer, odor-masking agent, oil, oil absorbent agent, ointment base, opacifier, organosilicone, oxidant, oxygen carrier, pearlant agent, perfume, perfume solvent, perfume stabilizer, peroxide stabilizer, pharmaceutical drug, photo-sensitizer agent, pigment, pigmenting agent, pearlescent aid, plant extract, plant derivative, plant tissue extract, plant root extract, plant seed extract, plant oil, plasticizer, polish agent, polymer, polymer film former, powder, preservative agent, propellant, peptide agent, protein agent, reducing agent, re-fatting agent, regenerator, resin, rosacea inhibitory agent, scar prevention agent, scalp agent, scrub agent, sabostatic agent, sequestrant, sex hormone, sex stimulating agent, silicone agent, silicone replacement agent, skin barrier agent, skin barrier restoration agent, skin calming agent, skin clarifier, skin cleanser, skin conditioning agent, skin exfoliating agent, skin peeling agent, skin healing agent, skin lipid, skin lightening agent, skin bleaching agent, skin protectant agent, skin purifier agent, skin smoothing agent, skin calming agent, skin soothing agent, skin sensate, skin treatment agent, skin penetration enhancing agent, skin penetration retarding agent, mucosa penetration enhancing agent, solubilizer, solvent, suspending agent, sun protection factor booster, soothing agent, spreading agent, stabilizer, stimulant agent, slimming agent, sunless tanning agent, sunscreen, sunscreen UVA, sunscreen UVB, broad-band sunscreen, super-fatting agent, surfactant, amphoteric surfactant, anionic surfactant, cationic surfactant, non-ionic surfactant, silicone surfactant, suspending agent, sweetener, tanning accelerator, thickening agent, thixotrope, tightening agent, toner, tonic agent, topical delivery system, vasoconstrictor agent, vulvar soothing agent, vaginal soothing agent, vegetable oil, volatile agent, viscosity stabilizer, vitamin, vaccine, water proofing agent, water-soluble agent, water-proofing agent, wax, wetting agent, whitening agent, wound healing agent, and/or the like.

Preferably, the additional ingredients should be suitable for use in contact with human keratinous tissue (hair, nails, skin, lips, external vulva (mons pubis, labia majora, labia minora)) and/or non-keratinous tissue (vagina, introitus, inner vulva (vulvar vestibule, clitoris), mouth, anus, etc.), without undue systemic toxicity local intolerability, and chemical instability.

In most instances, the additional substances will include a cosmetic, dermatologically, and/or pharmaceutically acceptable carrier either alone or in combination with still other additional (e.g., inert and/or biologically active) ingredients. The additional substances make up the balance of the composition.

Non-limiting examples of additional ingredients for some of the functional classes listed above are provided herein. Additional examples of additional ingredients can be found in The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known (and commonly used) in the art.

In order to be suitable for use in accordance with the present invention, the additional ingredients and carrier/excipients must be further chemically compatible with the topically acceptable silicone oil and/or non-silicone oil, Vitamin C (e.g., micronized L-ascorbic acid), Vitamin E (e.g., alpha-tocopherol), and/or the one or more polyphenol antioxidants. Here, "chemically compatible" means that the additional ingredients do not lead to a significant chemical degradation (e.g., hydrolysis, oxidation) of the antioxidants in the composition. For example, a significant chemical degradation would include more than 10% degradation during the shelf-life period (e.g., as provided by the expiration date) of the antioxidants in the composition under the recommended storage conditions of the product.

Peptides

The composition of the present invention can contain peptide(s). Suitable peptides can include, but are not limited to, di-, tri-, tetra-, penta-, hexa-peptides, and other oligo- to poly-peptides, and derivatives thereof.

For example, when included in the present compositions, the additional peptides are preferably used in amounts ranging from about 0.000001% to about 10%, more preferably from about 0.000001% to about 1%, and even more preferably from about 0.00001% to about 0.1% by weight of the composition. The exact content (%) of peptides to be used in the compositions will depend on the particular peptide utilized, since such agents vary widely in potency.

The peptides can be obtained from any supplier of commercially available cosmetic and pharmaceutical peptides, peptide mixtures or derivatives thereof; including but not limited to Atrium, Unipex, Lucas Meyer Cosmetics, Biotechnologies, Sederma, Croda, Grant Industries, Pentapharm, DSM, Evonik, Lipotec, Symrise, BASF, ISP, Helix BioMedix, Oriflame, Orpegen, Seppic, Solabia, Procyte, EMD Chemicals, Corium Peptides, etc.; or can be directly obtained by custom synthesis. When using commercially available cosmetic and pharmaceutical peptides, the preferred composition generally contains the additional peptide(s) in the concentration range as recommended by the peptide supplier.

A limited number of examples of peptides can be found in international patent application number PCT/US2014/018719, which is herein incorporated by reference in its entirety. Additional examples of suitable peptides can be also found in the chapter by F. Gorohhui and H. I. Maibach in the Textbook of Aging (2010, Springer), in Clinics in Dermatology 2009, 27, 485-495, or numerous other scientific articles, communications, patent applications, granted patents on peptides for cosmetic or medical uses (incorporated herein by reference).

Vitamin C Derivatives, Vitamin E Derivatives, and Other Vitamins

The compositions of the present invention may contain one or more derivatives, including but not limited to ascorbyl glucoside, ascorbyl palmitate, magnesium ascorbyl phosphate, sodium ascorbyl phosphate, tetrahexadecyl ascorbate, ascorbyl 3-aminopropyl phosphate, and other Vitamin C esters.

The compositions of the present invention may contain one or more Vitamin E derivatives, including, but not limited to, tocopheryl acetate, tocopherol sorbate, and other Vitamin E esters.

The compositions of the invention may contain one or more vitamins such as Vitamin B, Vitamin B derivatives, Vitamin B1 to Vitamin B12 and theirs derivatives, Vitamin K, Vitamin K derivatives, Vitamin H, Vitamin D, Vitamin D3, Vitamin D derivatives, and pro-vitamins thereof, such as panthenol and mixtures thereof. The vitamin compounds may be included as the substantially pure material, or as an extract obtained by suitable physical and/or chemical isolation from natural (e.g., plant) sources.

Sunscreen Actives

The compositions of the subject invention may optionally contain a sunscreen active. As used herein, "sunscreen active" includes both sunscreen agents and physical sunblocks. Suitable sunscreen actives may be organic or inorganic. A wide variety of conventional organic or inorganic sunscreen actives are suitable for use herein. In one example, the composition contains from about 0.1% to about 25%, more typically from about 0.5% to about 10% by weight of the composition, of the sunscreen active. Exact amounts will vary depending upon the sunscreen chosen and the desired Sun Protection Factor (SPF). The organic UV-screening agents which are more particularly preferred are chosen from the following compounds: ethylhexyl salicylate, butyl methoxydibenzoylmethane, ethylhexyl methoxycinnamate, octocrylene, phenylbenzimidazole sulphonic acid, terephthalylidene dicamphor sulphonic, benzophenone-3, benzophenone-4, benzophenone-5,4-methylbenzylidene camphor, benzimidazilate, anisotriazine, ethylhexyl triazone, diethylhexyl butamido triazone, methylene bis-benzotriazolyl tetramethylbutylphenol, drometrizole trisiloxane, bis-ethylhexyloxyphenol methoxyphenyl triazine, and mixtures thereof.

The inorganic sunscreen agents which may be used in the composition according to the invention are in particular nanopigments (mean size of the primary particles: generally between 5 nm and 100 nm, preferably between 10 nm and 50 nm; or their aggregates) of coated or uncoated metal oxides such as for example nanopigments of titanium oxide (amorphous or crystallized in the form of rutile and/or anatase), zinc oxide, zirconium or cerium oxides and mixtures thereof. Coating agents are moreover alumina and/or aluminum stearate, and silicones.

Anti-Wrinkle Actives and Anti-Atrophy Actives

The compositions of the present invention can contain one or more anti-wrinkle actives or anti-atrophy actives. Exemplary anti-wrinkle/anti-atrophy actives suitable for use in the compositions of the present invention include amino acids, N-acetyl derivatives of amino acids (e.g., N-acetylcysteine), hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid derivatives, retinoids (e.g., retinoic acid, tretinoin, isotretinoin, adapalene, retinol, retinyl-aldehyde, retinylpalmitate, and other retinoid derivatives), kinetin (N6-furfuryladenine), zeatin and their derivatives (e.g., furfurylamino-tetrahydropyranyladenine), niacinamide (nicotinamide); growth factors and cytokines (e.g., TGF-beta 1, 2 and 3, EGF, FGF-2, PDGF, IL-1, IL-6, IL-8, IGF-1, IGF-2, etc.), cell lysates (e.g., dermal fibroblast cell lysate, stem cell lysate, processed skin cell proteins (PSP®), etc.), conditioned cell culture mediums (e.g., conditioned cell culture medium from dermal fibroblasts, conditioned cell culture medium from stem cells (e.g., epidermal stem cells, adipose stem cells, mesenchymal stem cells, etc.); cosmetic ingredients marketed under the trade names Nouricel-MD®, TNS®, or CCM™ Complex; etc.); cell extracts, stem cell extracts, components from stem cells; ingredients stimulating epidermal or other human adult stem cells; skin conditioning agents, stilbenes, cinnamates, ingredients activating sirtuin 1 (e.g., resveratrol); ingredients improving the functioning of the mitochondria; dimethylaminoethanol, synthetic anti-aging peptides, peptides from natural sources (e.g., soy peptides), and salts of sugar acids (e.g., Mn gluconate, Zn gluconate), lipoic acid; lysophosphatidic acid, Vitamin B3 compounds, and other Vitamin B compounds (e.g., thiamine (Vitamin B1), pantothenic acid (Vitamin B5), riboflavin (Vitamin B2), and their derivatives and salts (e.g., HCl salts or calcium salts).

When anti-wrinkle/anti-atrophy compounds are present in the compositions of the instant invention, the compositions comprise from about 0.0001% to about 25%, more preferably from about 0.001% to about 10%, still more preferably from about 0.01% to about 5% by weight of the composition, of the anti-wrinkle/anti-atrophy compound. The exact content (%) of anti-wrinkle/anti-atrophy agents to be used in the compositions will depend on the particular anti-wrinkle/anti-atrophy agent utilized since such agents vary widely in potency.

Humectants, Moisturizers, and Conditioning Agents

Under certain circumstances, the compositions of the present invention can contain a safe and effective amount of a conditioning agent selected from, for example, humectants, moisturizers, and skin conditioners.

Humectants are ingredients that help maintain moisture levels in skin. Humectants can be selected from the group consisting of polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Additional humectants include acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed proteins, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, butylene glycol, sodium pyrollidone carboxylic acid (PCA), sorbitol, sucrose, dextran sulfate (i.e., of any molecular weight), natural moisturizing factors, and/or urea.

Skin conditioners can include, but are not limited to, guanidine, urea, glycolic acid, glycolate salts (e.g., ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, hexanetriol, butanetriol, propylene glycol, butylene glycol, hexylene glycol and the like, polyethylene glycols, propoxylated glycerols, sugars (e.g., melibiose), starches, sugar and starch derivatives (e.g., alkoxylated glucose, fructose, glucosamine), C1-C30 monoesters and polyesters of sugars and related materials, hyaluronic acid, lactamide monoethanolamine, acetamide monoethanolamine, panthenol, dexpanthenol, allantoin, and mixtures thereof. Skin conditioners can also include fatty acids, fatty acid esters, lipids, ceramides, cholesterol, cholesterol esters, bee wax, petrolatum, and mineral oil.

Emollients

Under certain circumstances, one or more emollients may also be included in the topical compositions described herein. An emollient generally refers to an ingredient that can help skin maintain a soft, smooth, and pliable appearance. Emollients typically remain on the skin surface, or in the stratum corneum, and act as a moisturizer, or lubricant and reduce flaking. Some examples of emollients include acetyl arginine, acetylated lanolin, algae extract, apricot kernel oil polyethylene glycol-6 esters, avocado oil polyethylene glycol-11 esters, bis-polyethylene glycol-4 dimethicone, butoxyethyl stearate, glycol esters, alkyl lactates, caprylyl glycol, cetyl esters, cetyl laurate, coconut oil polyethylene glycol-10 esters, alkyl tartrates, diethyl sebacate, dihydrocholesteryl butyrate, dimethiconol, dimyristyl tartrate, disteareth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, palm oil, coconut oil, myreth-3 palmitate, octyldecanol, octyldodecanol, odontella aurita oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, petrolatum, silicon oils including but not limited to caprylyl methicone, and/or tocopheryl glucoside.

Additional Antioxidants, and Radical Scavengers

The compositions of the present invention may include one or more additional antioxidant/radical scavengers such as beta-carotene, BHT, BHA, ferulic acid, ferulic acid esters, 6-hydroxy-2,5,7,8-tetramethylchroman-2-carboxylic acid (commercially available under the trade name Trolox™), gallic acid and its alkyl esters, especially propyl gallate, bioflavonoids, sulfhydryl compounds (e.g., glutathione), dihydroxy fumaric acid and its salts, silymarin, superoxide dismutase, lipoic acid, olive extracts, tea extracts, resveratrol, trans-resveratrol, polyphenols such as proanthocyanidine from pine bark, carotenoids, curcumin compounds such as tetrahydrocurcumin, coenzyme Q10, OCTA (L-2-oxo-4-thiazolidine carboxylic acid), selenium, glutathione, N-acetyl cysteine, N-acetyl cysteine esters, melanin; additional plant extracts containing polyphenols including but not limited to rosemary extracts, witch hazel extracts, and grape skin/seed extracts, may be used.

Antimicrobial Peptide Sequestering Agents

Antimicrobial peptide sequestering compounds may include but are not limited to a sulfated or polysulfated monosaccharide, and salts and complexes thereof; a sulfated or polysulfated disaccharide, and salts and complexes thereof; a sulfated or polysulfated polysaccharide, and salts and complexes thereof; a dextran sulfate (e.g., sodium dextran sulfate), and salts and complexes thereof; chondroitin sulfate, and salts and complexes thereof; pentosan polysulfate, and salts and complexes thereof; sucrose sulfate (e.g., any sucrose sulfate such as sucrose octasulphate other than aluminum sucrose sulfate), and salts and complexes thereof; a fucoidan, and salts and complexes thereof; a sulfated galactan, and salts and complexes thereof; a carrageenans (e.g., *Chondrus Crispus*), and salts and complexes thereof; starch sulfate, and salts and complexes thereof; cellulose sulfate, and salts and complexes thereof; a sulfated glycosaminoglycan, and salts and complexes thereof; a heparin; a heparan sulfate; sulfated glucan; or any combinations thereof. The antimicrobial peptide sequestering compound may include a plant extract, an algae extract, an aloe vera (barbadensis) extract, a cactus extract, or a shark or fish cartilage extract. The antimicrobial peptide sequestering compound may also be a sulfated or polysulfated polymer (e.g., poly(vinyl sulfate), poly(anethole sulfonate)). Suitable polymeric sulfonic acid that can be used in the methods and compositions described herein are hydrophobically modified polymeric sulfonic acids such as Aristoflex® HMP or Aristoflex® AVC (Clariant). Alternatively, the antimicrobial peptide sequestering compound is a phosphate or polyphosphate (e.g., a monosaccharide phosphate, a disaccharide phosphate, a polysaccharide phosphate, a glycerophosphate salt, or a starch phosphate). Suitable examples of starch phosphates include, but are not limited to hydroxypropyl starch phosphates (i.e., Structure XL (National Starch, LCC)). The antimicrobial peptide sequestering compound may also be a phospholipid such as phosphatidylcholine or lecithin. Further, the antimicrobial peptide sequestering compound can be a carboxylate, a polyhydroxy acid, hyaluronic acid, alginate, and/or polylactic acid. Most preferably, the antimicrobial peptide sequestering compounds are between 100 to 10,000 g per mol. Sodium dextran sulfate of about 5000 to 10,000 g per mol is one of the most preferred antimicrobial peptide sequestering compound.

Rosacea Inhibitory Agents, and α-Adrenergic Receptor Agonists

Rosacea inhibitory agents, include but are not limited to, metronidazole, sulfacetamide, sodium sulfacetamide, sulfur, dapson, doxycycline, minocycline, clindamycin, clindamycin phosphate, erythromycin, tetracylclines, azelaic acid, calcium dobesilate, maleic acid, and any compatible combinations thereof); α-adrenergic receptor agonists (e.g., clonidine, amphetamine, doxtroamphetamine, apraclonidine, dipivefrin, α-methyldopa, oxymetazoline, oxymetazoline hydrochloride, methoxamine, metaraminol, medetomidine, dexmedetomidine, ethylnorepinephrine, guanfacine, guanabenz, phenylephrine, phenylephrine hydrochloride, ephedrine, epinine, epinephrine, ethylnorepinephrine, levarterenol, lofexidine, norepinephrine, norphenylephrine, norephedrine, phenylpropanolamine, pemoline, propylhexadrine, pseudoephedrine, methamphetamine, α-methylnorepinephrine, methylphenidate, mephentermine, midodrine, mivazerol, moxonidine, desglymidodrine, tetrahydrozoline, tetrahydrozoline hydrochloride, cirazoline, amidephrine, brimonidine, brimonidine tartrate, naphazoline, isoproterenol, xylazine, xylometazoline, and/or tizanidine); chemicals and botanical extracts with vasoconstrictor properties including, but not limited to, corticosteroids, ephedrine, pseudoephedrine, caffeine, and/or escin; ephedra, *phedra sinica, hamamelis viginiana, hydrastis canadensis, lycopus virginicus, aspidosperma quebracho, cytisus scoparius, raphanus sativus* linn (radish leave extracts), horse chestnut extracts, etc., as well as any compatible combinations thereof; and/or a nasal and/or sinus decongestant.

Skin Lightening Agents, and Skin Bleaching Agents

The compositions of the present invention may contain a skin lightening agent. Suitable skin lightening agents include, but are not limited to, ascorbic acid and derivatives thereof; kojic acid and derivatives thereof; resorcinol and derivatives thereof (including but not limited to 4-ethyl resorcinol, 4-butyl resorcinol, 4-hexyl resorcinol, 4-octyl resorcinol, 4-decyl resorcinol, 6-methyl resorcinol, 6-ethyl resorcinol, 6-butyl resorcinol, 6-hexyl resorcinol, 6-octyl resorcinol, 6-decyl resorcinol, 4-phenylethyl resorcinol), retinoic acid and derivatives thereof (e.g., retinol, retinyl palmitate), L-leucine and derivatives thereof (e.g., N-acyl derivatives of L-leucine, esters of L-leucine, etc.), glycine and derivatives thereof, disodium glycerophosphate and derivatives thereof, undecenoyl phenylalanine, arbutin and derivatives thereof (e.g., dehydroxyarbutin), niacinamide and derivatives thereof, hydroquinone; mequinol, glabridin, aleosin, curcumin, genistein, ethyl linoleate, tranexaminic acid, azelaic acid, resveratrol and derivatives thereof (e.g., oxyresveratrol), N-acetyl glucosamine, 4-isopropylcetchol, 4-ethoxybenzaldehyde, 2-ethoxybenzaldehyde, 4-propoxybenzaldehyde, alpha-hydroxyacids (e.g., glycolic acid, lactic acid, etc.), salicylic acid, polyphenols; and/or various plant extracts, such as those from licorice, grape seed, mulberry, soy, green tea, and/or bear berry; and/or any ingredient or combination thereof.

When used, the compositions preferably contain from about 0.01% to about 15%, more preferably from about 0.1% to about 10%, also preferably from about 0.5% to about 5%, by weight of the composition, of a skin lightening agent. The exact content (%) of skin lightening agents to be used in the compositions will depend on the particular skin lightening agent utilized since such agents vary widely in potency.

Skin Protectants

Suitable skin protectant agents for use in the compositions described herein include, for example, a compound that protects injured or exposed skin or mucous membrane surfaces from harmful or irritating external compounds. Representative examples include algae extract, allantoin, *camellia sinensis* leaf extract, cerebrosides, dimethicone, glucuronolactone, glycerin, kaolin, lanolin, malt extract, mineral oil, petrolatum, white petrolatum, potassium gluconate, colloidal oat meal, calamine, cocoa butter, starch, zinc oxide, zinc carbonate, zinc acetate, and/or talc.

Desquamation Actives, Keratolytic Agents, and Peeling Agents

Under certain circumstances, a desquamating/keratolytic active may be added to the compositions of the present invention. In one example, the composition contains from about 0.01% to about 30%, preferably from about 0.1% to about 10%, more preferably from about 0.5% to about 5%, by weight of the composition, of a desquamating/keratolytic active. The exact content (%) of desquamating/keratolytic agents to be used in the compositions will depend on the particular desquamating/keratolytic agent utilized since such agents vary widely in potency.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids. Resorcinol and its low-molecular weight derivatives are other examples of useful keratolytic and/or desquamating agents.

Preferred keratolytic agents are selected from the group containing glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcinol, retinoic acid, adapalene, trichloroacetic acid, 5-fluoro uracil, azelaic acid. Keratolytic agents are also the salts, esters, possible cis- or trans-forms, racemic mixtures and/or the relative dextrorotatory or levorotatory forms of the above listed compounds. Such substances can be used singularly or in associations with each other.

Anti-Inflammatory Agents

An anti-inflammatory agent may be added to the compositions of the present invention. In one example, an anti-inflammatory agent is added at a level of from about 0.01% to about 10%, preferably from about 0.5% to about 5%, by weight of the composition. The exact content (%) of anti-inflammatory agents to be used in the compositions will depend on the particular anti-inflammatory agent utilized since such agents vary widely in potency.

Steroidal anti-inflammatory agents can include, but are not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, fluradrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. One of the preferred steroidal anti-inflammatory for use is hydrocortisone.

In addition, non-steroidal anti-inflammatory agents can be useful herein. The varieties of compounds encompassed by this group are well known to those skilled in the art. Specific non-steroidal anti-inflammatory agents that can be useful in the composition of the present invention include, but are not limited to, diclofenac, indomethacin, oxicams such as piroxicam, salicylates such as aspirin; acetic acid derivatives such as felbinac, fenamates such as etofenamate, flufenamic acid, mefenamic acid, meclofenamic acid, tolfenamic acid; propionic acid derivatives such as ibuprofen, naproxen, pyrazoles, and mixtures thereof. Mixtures of these non-steroidal anti-inflammatory agents may also be employed, as well as the dermatologically acceptable salts and esters of these agents. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), kola extract, chamomile, red clover extract, sea whip extract, licorice extract, and tea extract may be used.

Anti-inflammatory agents useful herein include allantoin and compounds of the Licorice, including glycyrrhetic acid, glycyrrhizic acid, and derivatives thereof (e.g., salts and suitable esters). Additional anti-inflammatory agents include diosgenol, saponines, sapogenines, lignanes, triterpenes saponosides and genines.

Additional examples of anti-inflammatory agents can include anti-inflammatory interleukins (e.g., IL-1ra, IL-10); anti-inflammatory fatty acids (e.g., linoleic acid, linolenic acid) and their derivatives (e.g., esters), isoprenylcystein analogues (i.e., N-acetyl-5-farnesyl-L-cysteine), aromatic aldehydes with anti-inflammatory properties (e.g., 4-methoxy benzaldehyde, 4-ethoxy benzaldehyde, 4-butoxy benzaldehyde, 4-penthoxy benzaldehyde), as well as any compatible combinations thereof.

Anti-Acne Actives

Under certain circumstances, the compositions of the present invention can contain one or more anti-acne actives. Examples of useful anti-acne actives include resorcinol, sulfur, erythromycin, salicylic acid, benzoyl peroxide, retinoic acid, tretinoin, alpha-hydroxy acids (e.g., glycolic acid, lactic acid), dehydroacetic acid and zinc. When anti-acne compounds are present in the compositions of the instant invention, the compositions contain from about 0.0001% to about 50%, more preferably from about 0.001% to about 20%, still more preferably from about 0.01% to about 10%, and still more preferably from about 0.1% to about 5%, by weight of the composition, of the anti-acne compound. The exact content (%) of anti-acne actives to be used in the compositions will depend on the particular antimicrobial, anti-bacterial and anti-acne active utilized since such agents vary widely in potency.

Antimicrobial, Anti-Bacterial and Anti Fungal Actives

The compositions of the present invention can contain one or more anti-fungal or anti-microbial actives. A safe and effective amount of an antimicrobial or antifungal active can be added to the present compositions. For example, the composition contains from about 0.001% to about 10%, preferably from about 0.01% to about 5%, and more preferably from about 0.05% to about 2%, by weight of the composition, of an antimicrobial or antifungal active. The exact content (%) of antimicrobial, anti-bacterial and anti-fungal actives to be used in the compositions will depend on the particular antimicrobial, anti-bacterial and anti-fungal active utilized since such agents vary widely in potency.

Suitable anti-microbial actives include, but are not limited coal to tar, sulfur, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, iodopropynyl butylcarbamate, azelaic acid, isothiazalinones such as octyl isothiazolinone and azoles, parabens (e.g., methylparaben, ethylparaben, etc.), glycols (e.g., hexylenglycol, ethylhexylglycerin), and combinations thereof.

For example, suitable agents with anti-fungal properties are ketoconazole, naftifine hydrochloride, oxiconazole nitrate, sulconazole nitrate, urea, terbinafine hydrochloride, selenium sulfide. Suitable agents with anti-mite properties are crotamiton, ivermectin, and permethrin.

Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol; and pharmaceutically acceptable salts thereof; benzyl alcohol, camphor, menthol, resorcinol; and appropriate combinations thereof.

Additional Plant, Fruit, and Vegetable Extracts

The compositions of the present invention may also contain a safe amount of other plant, fruit, or vegetable extracts. Examples of plant or vegetable extracts include extracts obtained from ivy (in particular English Ivy (*Hedera Helix*)), Chinese thorowax (*Bupleurum chinensis*), barley, *Bupleurum Falcatum*, arnica (*Arnica Montana* L), marigold (*Calendula officinalis*), sage (*Salvia officinalis* L), soy, ginseng (*Panax ginseng*), ginko biloba, St.-John's-Wort (*Hyperycum Perforatum*), butcher's-broom (*Ruscus aculeatus* L), European meadowsweet (*Filipendula ulmaria* L), big-flowered Jarva tea (*Orthosiphon Staminicus* Benth), algae (*Fucus Vesiculosus*), birch (*Betula alba*), green tea, white tea, fermented tea, cola nuts (*Cola Nipida*), horsechestnut, bamboo, spadeleaf (*Centella asiatica*), heather, fucus, willow, wild yam, mouse-ear, escine, cangzhu, chrysanthellum indicum, plants of the *Armeniacea* genus, *Atractylodis Platicodon, Sinnomenum, Pharbitidis, Flemingia, Coleus* such as *C. Forskohlii, C. blumei, C. esquirolii, C. scutellaroides, C. xanthantus* and *C. Barbatus*, root of *Coleus barbatus*, Ballote, Guioa, Davallia, Terminalia, Barringtonia, Trema, antirobia, cecropia, argania, dioscoreae such as *Dioscorea opposita* or Mexican, *Ammi visnaga, Centella asiatica* and *Siegesbeckia*, in particular *Siegesbeckia orientalis*, the family of Ericaceae in particular bilberry extracts (*Vaccinium angustifollium*) or Arctostaphylos uva ursi, aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum, Bacopa monieri* extract, sea whip, *Glycyrrhiza glabra*, mulberry, melaleuca (tea tree), mushroom extracts, Larrea divaricata, Rabdosia rubescens, euglena gracilis, Fibraurea recisa Hirudinea, Chaparral Sorghum, sun flower extract, Enantia chlorantha, Mitracarpe of *Spermacocea* genus, *Buchu barosma, Lawsonia inermis* L., *Adiantium Capillus-Veneris* L., *Chelidonium majus, Luffa cylindrical*, Japanese Mandarin (*Citrus reticulata* Blanco var. *unshiu*), broccoli extract, *Imperata cylindrical, Glaucium Flavum, Cupressus Sempervirens, Polygonatum multiflorum, loveyl hemsleya, Sambucus Nigra, Phaseolus lunatus, Centaurium, Macrocystis Pyrifera, Turnera Diffusa, Anemarrhena asphodeloides, Portulaca pilosa, Humulus lupulus, Coffee Arabica*, black berry, *Ilex Paraguariensis*; and so on.

Additional Oils and Lipids

Under certain circumstances (i.e., only if a composition according to the invention is reachable), the oil phase can contain any cosmetic or dermatological oil or a mixture thereof. Examples of such oils include but are not limited to aliphatic hydrocarbons such as liquid paraffin, squalene, squalane, vaseline and ceresin; vegetable oils such as avocado oil, apricot oil, almond oil, borage oil, borage seed oil, camellia oil, canola oil, castor oil, coconut oil, cocoa butter, corn oil, cottonseed oil, olive oil, evening primrose oil, flax seed oil, palm oil, palm kernel oil, peanut oil, rapeseed oil, safflower oil, sesame oil, sweet almond oil, rose hip oil, *calendula* oil, chamomile oil, eucalyptus oil, juniper oil, safflower oil, sandalwood oil, tea tree oil, sunflower oil, soybean oil, wheat germ oil; animal oils such as shark liver oil, cod liver oil, whale oil, beef tallow and butterfat; waxes such as beeswax, carnauba palm wax, spermaceti and lanolin; fatty acids such as lauric acid, myristic acid, palmitic, acid, stearic acid, oleic acid, behenic acid; omega-3 fatty acids such as alpha-linolenic acid, eicosapentaenoic acid, and docosahexaenoic acid; omega-6 fatty acids such as linoleic acid and gamma-linolenic acid; aliphatic alcohols such as lauryl, stearyl, cetyl, and oleyl alcohol; and aliphatic esters such as isopropyl, isocetyl, or octadecyl myristate, butyl stearate, hexyl laureate, diisopropyl ester of adipic acid, or diisopropyl sebacate; and/or mixtures thereof. Generally, the oils are refined and/or hydrogenated. Lipids include monoglycerides, diglycerides, triglycerides, phospholipids, and ceramides.

Suspending Agents

The compositions of the present invention may further contain a suspending agent, preferably at concentrations effective for suspending water-insoluble material in dispersed form in the compositions or for modifying the viscosity of the composition. Such concentrations can preferably range from about 0.1% to about 10%, more preferably from about 0.25% to about 5.0%. Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Other optional suspending agents include crystalline suspending agents which can be categorized as acyl derivatives, long chain amine oxides, long chain acyl derivatives and mixtures thereof. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin). Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Emulsifying Agents

Under certain circumstances (i.e., only if a composition according to the invention is reachable), emulsifying agents can be added in order to obtain a composition in accordance with the present invention. Emulsifying agents include a wide variety of nonionic, cationic, anionic, zwitterionic, and amphoteric surfactants such as are known in the art and discussed below. The hydrophilic surfactants (cationic, anionic, zwitterionic, amphoteric) useful herein can contain a single surfactant, or any combination of suitable surfactants. The exact surfactant (or surfactants) chosen will depend upon the pH of the composition and the other components present.

Useful nonionic surfactants include the condensation products of alkylene oxides with fatty acids (i.e., alkylene oxide esters of fatty acids), the condensation products of alkylene oxides with 2 moles of fatty acids (i.e., alkylene oxide diesters of fatty acids), the condensation products of alkylene oxides with fatty alcohols (i.e., alkylene oxide ethers of fatty alcohols), the condensation products of alkylene oxides with both fatty acids and fatty alcohols [i.e., wherein the polyalkylene oxide portion is esterified on one end with a fatty acid and etherified (i.e., connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof. Still other useful nonionic surfactants include polyhydroxy fatty acid amide surfactants. An especially preferred surfactant corresponding to the above structure is coconut alkyl N-methyl glucoside amide. Preferred among the nonionic surfactants are those selected from the group consisting of steareth-21, ceteareth-20, ceteareth-12, sucrose cocotte, steareth-100, PEG-100 stearate, and mixtures thereof. Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof. Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the trade name Arlatone 2121.

Also useful herein are cationic surfactants, especially dialkyl quaternary ammonium compounds. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride. Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow)dimethyl ammonium chloride, di(hydrogenated tallow)dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride. More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof. A preferred combination of cationic surfactant and structuring agent is behenamidopropyl PG dimonium chloride and/or behenyl alcohol, wherein the ratio is preferably optimized to maintain or to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethionic acid and neutralized, i.e., the alkoyl isethionates typically have the formula RCOOCH2CH2SO3M wherein R is alkyl or alkenyl of from about 10 to about 30 carbon atoms, and M is a water-soluble cation such as ammonium, sodium, potassium and triethanolamine. For example, the fatty acids are derivated from coconut or palm kernel oil. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. The alkyl and alkyl ether sulfates typically have the respective formulae ROSO3M and RO(C2H4O)xSO3M, wherein R is alkyl or alkenyl of from about 10 to about 30 carbon atoms, x is from about 1 to about 10, and M is a water-soluble cation such as ammonium, alkanolamines such as triethanolamine, monovalent metals, such as sodium and potassium, and polyvalent metal cations such as magnesium and calcium. Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized. Another suitable class of anionic surfactants are the water-soluble salts of the organic, sulfuric acid reaction products of the general formula R1-SO3-M, wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and beta-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. Another class of anionic surfactants suitable for use in the compositions is the beta-alkyloxy alkane sulfonate class. Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH(CH2)mCO2M wherein m is from 1 to 4, R is a C8-C22 alkyl or alkenyl, and M is H, alkali metal, alkaline earth metal ammonium, or alkanolammonium. Preferred amphoteric surfactants for use in the present invention include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate; N-higher alkyl aspartic acids; and the products sold under the trade name "Miranol". Other examples of useful amphoterics include phosphates, such as coamidopropyl PG-dimonium chloride phosphate (commercially available as Monaquat PTC, from Mona Corp.). Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl)carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel). Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Thickening Agents

Thickening agents suitable for inclusion in a composition described herein include those agents commonly used as an excipient or a carrier for topical application to increase the viscosity of the formulation. Thickening agents may also be used to improve the stability of the formulation and the product.

More specifically, such examples include but are not limited to, acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxylethyl-cellulose, hydroxypropylcellulose, hydroxypropyl starch, magnesium alginate, methylcellulose, microcrystalline cellulose, pectin, various polyethylene glycol's, polyacrylic acid, poly-methacrylic acid, polyvinyl alcohol, various polypropylene glycols, sodium acrylates copolymer, sodium carrageenan, xanthan gum, and/or yeast beta-glucan.

More generally, carboxylic acid polymers useful thickening agents. Carboxylic acid polymers are cross-linked compounds containing one or more monomers derived from acrylic acid, substituted acrylic acids, and salts and esters of these acrylic acids and the substituted acrylic acids, wherein the cross-linking agent contains two or more carbon-carbon double bonds and is derived from a polyhydric alcohol. Examples of commercially available carboxylic acid polymers useful herein include the carbomers, which are homopolymers of acrylic acid cross-linked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of C10-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-30 alkyl acrylate crosspolymers and are commercially available as Carbopol® 1342, Carbopol® 1382, Pemulen TR-1, and Pemulen TR-2, from B.F. Goodrich. Examples of preferred carboxylic acid polymer thickeners useful herein include those selected from carbomers, acrylates/C10-30 alkyl acrylate crosspolymers, and mixtures thereof.

Moreover, a wide variety of polysaccharides are useful herein as thickening agents. Non-limiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10-30 straight chain or branched chain alkyl group through an ether linkage. Typically these polymers are ethers of C10-30 straight or branched chain alcohols with hydroxyalkylcelluloses. Examples of alkyl groups useful herein include those selected from stearyl, isostearyl, lauryl, myristyl, cetyl, isocetyl, cocoyl (e.g., alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the trade name Natrosol® CS Plus from Aqualon Corporation (Wilmington, Del.). Additional examples can be found in The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art. Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, dextran sulfate, sodium carrageenan, tragacanth gum, xanthan gum, and/or mixtures thereof. In addition, the compositions of the present invention can also optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the trade name Sepigel 305 from Seppic Corporation (Fairfield, N.J.). Other polyacrylamide polymers useful herein include multi-block copolymers of acrylamides and substituted acrylamides with acrylic acids and substituted acrylic acids.

Preferred compositions of the present invention include a thickening agent selected from carboxylic acid polymers, cross-linked polyacrylate polymers, polyacrylamide polymers, and mixtures thereof, more preferably selected from carboxylic acid polymers, polyacrylamide polymers, and mixtures thereof.

Penetration Enhancers

Penetration enhancers are the substances that facilitate the absorption of penetrant through the skin or mucosal membranes by temporarily diminishing the impermeability of the skin or, respectively, the mucosa. Ideally, these materials should be pharmacologically inert, nontoxic, nonirritating, non-allergenic, compatible, odorless, tasteless, colorless, and inexpensive and have good solvent properties. The enhancer should not lead to the significant loss of body fluids, electrolytes, and other endogenous materials, and skin or mucosa should regain its barrier properties on its removal within an acceptable period of time. No single penetration enhancer can possess all the required properties. However, many enhancers exhibit many of these attributes, and they have been described (for example as reviewed in Drug Development and Industrial Pharmacy 2000, 26, 1131-1140) or are being currently researched.

Anti-Histamines

Anti-histamines, also called histamine antagonists, are substances that inhibit the action of histamine by blocking it from attaching to histamine receptors; or by inhibiting the enzymatic activity of histidine decarboxylase, catalyzing the transformation of histidine into histamine; or the like. Examples of anti-histamines are acrivastine, azelastine, brompheniramine, buclizine, bromodiphenhydramine, carbinoxamine, cetirizine, chlorpromazine, cyclizine, chlorpheniramine, chlorodiphenhydramine, cimetidine, clemastine, cyproheptadine, desloratadine, dexbrom-pheniramine, deschlorpheniramine, dexchlorpheniramine, dimenhydrinate, dimetindene, diphenhydramine, doxylamine, ebastine, embramine, famotidine, fexofenadine, lafutidine, levocetirizine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tripelennamine, and triprolidine.

For example, the use of one or more suitable anti-wrinkling substance (e.g., retinoic acid, retinol, transforming growth factor beta-1, selected peptides, etc.) will increase the clinical efficacy (e.g., reduced skin wrinkles) of the antioxidant compositions after topical administration; the use of one or more suitable emollient substance (e.g., octyldodecanol, etc.) will increase the clinical efficacy (e.g., improved skin feel or sensations) of the antioxidant composition after topical administration; the use of one or more suitable humectant substance (e.g., glycerin, hyaluronic acid, etc.) will increase the clinical efficacy (e.g., increased skin moisturization) of the antioxidant composition after topical administration; the use of one or more suitable skin penetration enhancer substance (e.g., propylene glycol, butylene glycol, ethanol, oleic acid, lauric acid, palmitic acid, isopropyl palmitate, DMSO, sodium lauryl sulfate, Azone®, etc.) will increase the clinical efficacy (e.g., reduced skin wrinkles) of the antioxidant composition after topical administration; the use of one or more suitable anti-inflammatory substance (e.g., bisabolol, glycyrrhetinic acid, linoleic acid, borage seed oil, wheat germ oil, etc.) will increase the clinical efficacy (e.g., reduced irritation or redness of skin or mucosa) of the antioxidant composition after topical administration; the use of one or more suitable topical anesthetic substance (e.g., lidocaine, pramoxine hydrochloride, etc.) will increase the clinical efficacy (e.g., reduced local pain) of the antioxidant composition after topical administration; and/or the use of one or more suitable topical anti-histamine substance (e.g., diphenhydramine, etc.) will increase the clinical efficacy (e.g., reduced local itch) of the antioxidant composition.

Carriers and Excipients

The compositions of the present invention can also contain one or more carriers and/or excipients acceptable for a mode of administration (i.e., for topical application and/or for subcutaneous administration). Those skilled in the art will be able to routinely select an appropriate carrier and/or excipient for the mode of administration. Depending in the use and the way of administration, the compositions of the present invention can also contain carrier(s) and/or excipient(s) acceptable for injection, implantation, or subcutaneous placement.

The carrier and/or excipient can be in a variety of forms. Non-limiting examples of suitable carriers and/or excipients include simple substantially free of water based solutions in oils (i.e., silicon oils or non-silicon oils); substantially free of water based emulsions of oils in glycols (e.g., propylene glycol, butylene glycol, PEGs, etc.); substantially free of water based dispersions in oils; water free two-phase (e.g., solid and liquid) systems; substantially free of water based semi-solid forms (e.g., serums, ointments, etc.); substantially free of water based solid forms (e.g., powder, sticks, patches); substantially free of water based skin masks;

substantially free of water based tissues; substantially free of water based foams; and substantially free of water based aerosols.

Composition Preparation

The compositions of the present invention are generally prepared by conventional methods such as are known in the art of making compositions suitable for topical application. Such methods can typically be conducted in one or more steps, with or without heating, cooling, and the like.

In addition, the compositions of the present invention can also be prepared by conventional methods such as are known in the art of making compositions suitable for injections.

As used herein, a "formulation" is a mixture prepared according to a specific procedure.

The physical form of the compositions according to the invention is not important. They may be in galenic form such aerosols, creams, lotions, milk or cream ointments, gels, emulsions, dispersions, solutions, suspensions, cleansers, foundations, anhydrous preparations (sticks, in particular lip balm, body and bath oils), and scalp treatment lotions, cream or lotion for care of skin or hair, solution for care of skin or hair, cream or lotion for care of the genitals (e.g., vulva, vagina, penis, scrotum), gel or solution for care of genitals, make-up removing lotions or creams, sunscreen lotions, milks, artificial suntan lotions; pre-shave, shave or after shave creams, foams, gels or lotions; make-up, lipsticks, mascaras or nail varnishes; skin essences, serums; adhesive or absorbent materials, skin masks; tissues; patches, transdermal patches, iontophoretic patches, microneedle patches; powders; emollient lotion, sprays, oils for the body and the bath, foundation tint bases, pomade, colloid, compact or solid suspension, pencil, sprayable or brossable formulation, blush, rouge, eyeliner, lip liner, lip gloss, facial or body powder, mousse or styling gels, nail conditioner, lip balms, skin conditioners, anorectal creams, hygiene cream, moisturizers, hair sprays, hair conditioners, soaps, body exfoliants, astringents, depilatories and permanent waving solutions, anti-dandruff formulations, anti-hair loss formulations, anti-sweat and anti-perspirant formulations, nose sprays; and so on.

These compositions can also be presented in the form of lipsticks intended to apply color or to protect the lips from cracking, or of make-up products for the eyes or tints and tint bases for the face. Compositions in accordance with the invention include cosmetics, personal care products, feminine products, male products, hygiene products, and dermatological or pharmaceutical preparations.

The compositions of the present invention may also be applied on animal skin.

The compositions according to the present invention may be prepared in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes, cubosomes; macro-, micro-, or nanoparticles; or macro-, micro or nanosponges; or macro-, micro-, and nanocapsules; or macro-, micro- or nanospheres; micro- or nano-emulsions; or adsorbed onto tip of needles; or adsorbed onto microneedles or onto microneedle arrays; or adsorbed to organic polymer powders, talcs, bentonites, or other inorganic or organic supports.

Furthermore, the compositions according to the present invention may be used in any form whatsoever, in a form bound to or incorporated in or absorbed in or adsorbed on macro-, micro-, and nanoparticles; or macro-, micro or nanosponges; or macro-, micro-, and nanocapsules; or macro-, micro- or nanospheres; or adsorbed (e.g., by coating) onto microneedle patches or arrays (such as described by Ameri M. et al., Pharm Res 2010, 27: 303-313); for the treatment of textiles, natural or synthetic fibers, wools, and any materials that may be used for clothing or underwear for day or night intended to come into contact with the skin, handkerchiefs or cloths, to exert their effect via this skin/textile contact and to permit continuous topical deliver.

The compositions according to the present invention may also be prepared or used in a form of a device (e.g., medical device, combination between drug and medical device). Preferred devices include, but are not limited to, devices for overcoming biological barriers such as ultrasound devices (i.e., sonophoresis, sonoporation, acoustic ablation), electric devices (iontophoresis, electroporation), high pressure devices (i.e., liquid injection, powder injection), microneedles (i.e., solid, hollow, degradable, coated), thermal and optical devices (i.e., light, infrared, laser, radiofrequency), other physical devices reducing the skin barrier (i.e., plasma devices, micro-dermabrasion, dermabrasion, suction devices, macro-needle devices, etc.), devices reducing the skin barrier by chemical means (i.e., chemical exfoliating devices, skin corrosion (e.g., using NaOH) devices), and/or any combination or combination device thereof. Some example of methods and devices for overcoming biological barriers have been described in Advanced Drug Delivery Reviews 2013, 65, 100-103 (incorporated herein as reference).

In addition, the compositions according to the present invention may be used in any form intended to be placed into the skin or mucosal tissue, or under the skin or mucosal tissue (e.g., by injection, implantation, or subcutaneous placement).

Method of Treatment

The present invention concerns compositions for their application as a cosmetic, personal care, or a medicinal product.

The composition according to the invention can be applied topically onto any areas of the face, neck, neckline, décolleté, scalp, hand, palm, arm, leg, foot, sole, chest, breast, back, abdomen, buttock, vulva, or penis and scrotum, anus, and/or any other skin areas of the human body.

Further, the composition according to the invention can be also applied locally or topically onto any areas of the eye, mouth, nose, breast nipples, vulva, vagina and introitus; or penis and scrotum; rectum, and/or any other mucosal areas of the human body.

Furthermore, the composition according to the invention can also be applied locally or topically to other surfaces of the human body, including hair and nail, or any wound, scar, or skin and mucosal surface areas affected by atrophy, or other conditions, disorders and diseases associated with free radical related skin damage.

In addition, the compositions according to the present invention may also be applied by injection, implantation, or subcutaneous placement.

For example, the compositions described herein can be applied using a syringe, a micro-cannula, a patch, an iontophoretic patch, microneedles, and/or a microneedle array or patch. In addition, the composition can be also applied in conjunction (i.e., before, after, or simultaneously) with the use of other skin devices changing the penetration characteristics of skin such as, for example, laser, light, infrared, radiofrequency, ultrasound, electroporation, sonophoresis, thermal, plasma, and/or high pressure devices, and/or any combination(s) (including combination devices) thereof. Any other commonly used means of administration can also be utilized.

In addition, the compositions according to the present invention may also be applied in animals.

In one example, the present invention concerns treatment methods to improve with free radical related skin damage involving topical application of an effective amount of the composition as defined above to the skin. More specifically, these methods can be used to treat, alleviate, and/or ameliorate a symptom, condition, disorder, and/or disease associated with free radicals. For example, the symptom, condition, disorder and/or disease may include sun induced skin damages, electromagnetic radiation (visible light, UV, IR) induced skin damages, air pollution induced skin damages, smoking induced skin damages, skin aging, skin inflammatory diseases or disorders, skin degenerative diseases or disorders, nutrition induced skin damages, metabolism induced skin damages, and cancer. The compositions may neutralize free radicals.

Such methods typically require the repeated topical or subcutaneous administration of the composition. Some benefits can be noticed within a few hours to a few days after topically applying the compositions according to the present invention on the affected human skin or human tissue. However, it takes generally at least 30 days to notice benefits. Thereby, the composition should be applied to the affected human skin or human tissue at least once to twice a day for at least 30 days.

Also provided are methods of modifying free radical damage to skin by administering an effective amount of any of the antioxidant compositions of the invention to the skin of a patient. Ideally, the effective amount is sufficient to treat, prevent, or treat and prevent free radical damage to the skin.

Determination of an effective dose or amount (e.g., therapeutically, cosmetically, pharmaceutically, and/or medicinally effective dose) of any of the compositions of the instant invention is within the routine level of skill in the art.

Kits and Dosage Forms

According to the invention, products or devices with several compartments or kits (having one or more containers) may be proposed to apply the compositions of the invention. By way of non-limiting example, a first compartment or container having antioxidant compositions of the invention and one or more additional substances (e.g., one or more biologically active ingredients and/or one or more inactive ingredients such as an excipient and/or a carrier) in a second compartment or container, the compositions contained in the said first and second compartments in this case being considered to be a combination composition for simultaneous, separate or step-wise use in time, particularly in any one of the treatments defined above. Alternatively, kits according to the invention may include the components of the compositions in separate compartments or containers or certain components can be in the same compartments or containers while others are in separate compartments or containers. Such kits will also preferably include instructions for use.

Any of the compositions described herein may be supplied in dosage unit form for ease of administration and uniformity of dosage. Dosage unit form as used herein refers to physically discrete units suited as unitary dosages for the mammalian subjects to be treated; each unit containing a predetermined quantity of the antioxidant composition according to the invention calculated to produce the desired cosmetic, personal care or therapeutic effect in association with the required cosmetic and/or pharmaceutical carrier(s). The specification for the dosage unit forms of the invention are dictated by and directly dependent on (a) the unique characteristics of the compositions and the particular maintenance, therapeutic or prophylactic effect to be achieved, and (b) the limitations inherent in the art of compounding for the treatment of individuals.

The unit dosage form is any of a variety of forms, including, for example, but not limited to, a solution, any semi-solid form, a capsule, a bag, a tablet, a single pump on an aerosol or a vial. The quantity of active ingredient(s) in a unit dose of composition is an effective amount and is varied according to the particular treatment involved.

One skilled in the art will appreciate that it is sometimes necessary to make routine variations to the dosage depending on the age and condition of the patient. The dosage will also depend on the route of administration.

EXAMPLES

Examples of suitable composition(s) and their preparation are described hereafter. These compositions and their preparation is representative of, but does not restrict, the scope of the invention.

The Examples set forth herein are meant to exemplify the various aspects of carrying out the invention and is not intended to limit the invention in any way. Unless otherwise specified, it is to be understood that the concentrations of the ingredients in the compositions of the invention are in weight percentages (w %), based on the total weight of the composition. All measurements are performed at 25° Celsius unless stated otherwise.

The following Examples describe and demonstrate various aspects within the scope of the present invention. The Examples are only given for illustrative purposes and should not be considered to be restrictive to this invention.

Each of the Examples provided herein clearly indicate that an antioxidant product formulated with 15% ascorbic acid and 1% α-tocopherol combined with epigallocatechin gallate, dimethylmethoxy chromanol and creatine in a silicone based, water-free formulation helps limit oxidative stress and its biochemical and clinical consequences.

Example 1

Preparation of Antioxidant Composition I

This Example illustrates the preparation of an antioxidant composition in accordance to the present invention. However, the person of skill in the art will understand that any other suitable methods can also be used to prepare compositions in accordance with the instant invention.

The compositions can be filled into suitable packaging (containers) such as, for example, tubes, pumps, airless pumps, jars, bottles, pens, aerosol containers, or other containers depending on use and administration. The compositions are generally commercialized in those containers.

Composition I:

| # | Ingredient(s) | Trade Name | Ingredient Manufacturer/ Supplier | Phase | Percentage (w/w) |
|---|---|---|---|---|---|
| 1 | CYCLOPENTASILOXANE, ASCORBIC ACID, POLYSILICONE-11, ETHYLHEXYL HYDROXYSTEARATE | GRANACTIVE AA-20 | GRANT INDUSTRIES, INC. | A | 76.50000% |
| 2 | DIMETHICONE | DC FLUID 200/05 CST | DOW CORNING CORP | A | 7.850000% |
| 3 | CYCLOPENTASILOXANE, DISTEARDIMONIUM HECTORITE, PROPYLENE CARBONATE | BENTONE GEL VS 5 PCV | ELEMENTIS SPECIALTIES | A | 5.000000% |
| 4 | PROPANEDIOL | ZEMEA PROPANEDIOL | DUPONT | B | 3.000000% |
| 5 | GLYCERIN | GLYCERIN USP | PROCTOR & GAMBLE | B | 1.000000% |
| 6 | DIMETHYLMETHOXY CHROMANOL | LIPOCHROMAN ES290 | LIPOTEC | B 1 | 0.050000% |
| 7 | EPIGALLOCATECHIN GALLATE | TEAVIGO (EGCG) | DSM FINE CHEMICALS INC. | B 1 | 0.100000% |
| 8 | CREATINE | TEGO COSMO C 100 | EVONIK | B 1 | 0.500000% |
| 9 | CETYL PEG/PPG-10/1 DIMETHICONE | ABIL EM90 | EVONIK | C | 5.000000% |
| 10 | TOCOPHEROL | DL-ALPHA TOCOPHEROL | DSM FINE CHEMICALS INC. | D | 1.00000% |

Such a composition can generally be prepared in a clean and sanitized stainless steel vessel as described herein below:

PHASE A PREMIX PHASE A AND MIX UNTIL UNIFORM. HOMOGENIZE FOR 10 MINS AT 3000 RPM

PHASE B PREMIX PHASE B

PHASE B1 ADD EACH INGREDIENT IN PHASE B1 TO PHASE B ONE AT A TIME AND HEAT TO 40° C. WITH MIXING UNTIL ALL THE POWDERS DISSOLVE

PHASE C SLOWLY ADD PHASE B/B1 TO PHASE C AND MIX UNTIL UNIFORM

PHASE D ADD PHASE D TO PHASE B/C AND MIX UNTIL UNIFORM SLOWLY ADD PHASE B/C/D TO PHASE A AND MIX UNTIL UNIFORM HOMOGENIZE FOR 5 MINS AT 3000 RPM ON SILVERSON USING SMALL HOLES

Example 2a

Glycol Free Preparation of Antioxidant Composition

| # | Ingredient(s) | Trade Name | Ingredient Manufacturer/ Supplier | Phase | Percentage (w/w) |
|---|---|---|---|---|---|
| 1 | CYCLOPENTASILOXANE, ASCORBIC ACID, POLYSILICONE-11, ETHYLHEXYL HYDROXYSTEARATE | GRANACTIVE AA-20 | GRANT INDUSTRIES, INC. | A | 76.50000% |
| 2 | DIMETHICONE | DC FLUID 200/05 CST | DOW CORNING CORP | A | 8.850000% |
| 3 | CYCLOPENTASILOXANE, DISTEARDIMONIUM HECTORITE, PROPYLENE CARBONATE | BENTONE GEL VS 5 PCV | ELEMENTIS SPECIALTIES | A | 5.000000% |
| 4 | GLYCERIN | GLYCERIN USP | PROCTOR & GAMBLE | B | 3.000000% |
| 5 | DIMETHYLMETHOXY CHROMANOL | LIPOCHROMAN ES290 | LIPOTEC | B 1 | 0.050000% |
| 6 | EPIGALLOCATECHIN GALLATE | TEAVIGO (EGCG) | DSM FINE CHEMICALS INC. | B 1 | 0.100000% |
| 7 | CREATINE | TEGO COSMO C 100 | EVONIK | B 1 | 0.500000% |
| 8 | CETYL PEG/PPG-10/1 DIMETHICONE | ABIL EM90 | EVONIK | C | 5.000000% |
| 9 | TOCOPHEROL | DL-ALPHA TOCOPHEROL | DSM FINE CHEMICALS INC. | D | 1.00000% |

Such a composition can generally be prepared in a clean and sanitized stainless steel vessel as described herein below:

PHASE A PREMIX PHASE A AND MIX UNTIL UNIFORM. HOMOGENIZE FOR 10 MINS AT 3000 RPM
PHASE B PREMIX PHASE B
PHASE B1 ADD EACH INGREDIENT IN PHASE B1 TO PHASE B ONE AT A TIME AND HEAT TO 40° C. WITH MIXING UNTIL ALL THE POWDERS DISSOLVE
PHASE C SLOWLY ADD PHASE B/B1 TO PHASE C AND MIX UNTIL UNIFORM
PHASE D ADD PHASE D TO PHASE B/C AND MIX UNTIL UNIFORM SLOWLY ADD PHASE B/C/D TO PHASE A AND MIX UNTIL UNIFORM HOMOGENIZE FOR 5 MINS AT 3000 RPM ON SILVERSON USING SMALL HOLES

Example 2b

Glycol and Glycerin Free Preparation of Antioxidant Composition

| # | Ingredient(s) | Trade Name | Ingredient Manufacturer/ Supplier | Phase | Percentage (w/w) |
|---|---|---|---|---|---|
| 1 | CYCLOPENTASILOXANE, ASCORBIC ACID, POLYSILICONE-11, ETHYLHEXYL HYDROXYSTEARATE | GRANACTIVE AA-20 | GRANT INDUSTRIES, INC. | A | 76.50000% |
| 2 | DIMETHICONE | DC FLUID 200/05 CST | DOW CORNING CORP | A | 11.850000% |
| 3 | CYCLOPENTASILOXANE, DISTEARDIMONIUM HECTORITE, PROPYLENE CARBONATE | BENTONE GEL VS 5 PCV | ELEMENTIS SPECIALTIES | A | 5.000000% |
| 4 | DIMETHYLMETHOXY CHROMANOL | LIPOCHROMAN ES290 | LIPOTEC | B | 0.050000% |
| 5 | EPIGALLOCATECHIN GALLATE | TEAVIGO (EGCG) | DSM FINE CHEMICALS INC. | B | 0.100000% |
| 6 | CREATINE | TEGO COSMO C 100 | EVONIK | B | 0.500000% |
| 7 | CETYL PEG/PPG-10/1 DIMETHICONE | ABIL EM90 | EVONIK | C | 5.000000% |
| 8 | TOCOPHEROL | DL-ALPHA TOCOPHEROL | DSM FINE CHEMICALS INC. | D | 1.00000% |

Such a composition can generally be prepared in a clean and sanitized stainless steel vessel as described herein below:

PHASE A PREMIX PHASE A AND MIX UNTIL UNIFORM. HOMOGENIZE FOR 10 MINS AT 3000 RPM
PHASE B/C ADD EACH INGREDIENT IN PHASE B TO PHASE C ONE AT A TIME AND HEAT TO 40° C. WITH MIXING UNTIL ALL THE POWDERS DISSOLVE
PHASE D ADD PHASE D TO PHASE B/C AND MIX UNTIL UNIFORM SLOWLY ADD PHASE B/C/D TO PHASE A AND MIX UNTIL UNIFORM HOMOGENIZE FOR AT LEAST 15 TO 30 MINS AT 3000 RPM ON SILVERSON USING SMALL HOLES

Example 3

Antioxidant Capacity In Vitro (i.e., in a Bottle) for an Antioxidant Serum with 15% Micronized Ascorbic Acid and Combination of Additional Antioxidants Introduction:

A novel antioxidative capacity method was used to determine the activity of antioxidants by following the reducing activity against a semi-stable test radical by Electron Spin Resonance (ESR) spectroscopy as described in Spectrochim Acta A Mol. Biomol. Spectrosc. 63, 2006, 846-850, which is herein incorporated by reference. Since this spectroscopic technique is able to directly quantify free radicals and since it is applicable to opaque, viscous, and colored samples, it is particular suitable for the analysis of antioxidants in cosmetic products, which is not possible with the Oxygen Radical Absorbance Capacity (ORAC) method. Both the reaction time and the reduction potential of the antioxidants contribute to the calculation of the antioxidative power (AP). The resulting AP is expressed in so called Antioxidative Units (AU), where 1 AU corresponds to the activity of a 1 ppm solution of L-ascorbic acid as a benchmark.

Materials and Methods:

The measurements were performed with the X-band ESR spectrometer Miniscope MS 300 (Magnettech, Germany) at the following settings: 60 G sweep width, 100 Gain, 1 G modulation amplitude, 7 mW attenuation, 3365 G central field, and 0.14 sec time constant. The test radical 2,2-diphenyl-1-picryl-hydrazyl (DPPH; a nitroxide probe) was obtained from Sigma-Aldrich, Munich, Germany. At least three concentrations of each of the antioxidant test samples were prepared and added to DPPH to obtain an initial concentration of 0.1 mM DPPH. The signal intensity decay of each concentration of the test samples was recorded at different time intervals during the reaction until completion of the reaction with the test radical. A first order kinetic of the decay of the ESR signal intensity was obtained for each concentration what allowed to calculate the reaction time $t_r$. The static parameters were used to calculate the characteristic weight $w_c$. Both parameters were used to calculate the AP by means of the following equation:

$$AP = RA \times N_{DPPH}/t_r \times w_c.$$

In order to compare between different antioxidants, the AP measure was standardized to the activity of L-ascorbic acid (obtained at the highest purity from Sigma-Aldrich, Munich, Germany). The antioxidative activity of a solution of 1 ppm Vitamin C was defined as one Antioxidative Unit (AU). Each AP value was the result of three independent measurements.

The following five different antioxidant products were evaluated (see Table 3). Only Product A is a composition according to the present invention.

TABLE 3

| Product | Ascorbic Acid | Tocopherol | Phenol or Polyphenol Antioxidants | Additional Antioxidants |
| --- | --- | --- | --- | --- |
| A | 15% | 1% | EGCG (Epigallocatechin Gallate) | Dimethylmethoxy Chromanol, Creatine |
| B | 15% | 1% | Ferulic Acid | Not present |
| C | 10% | 1% | Not present | Tetrahexyldecyl Ascorbate, Tocopheryl Acetate |
| D | Not present | Present | Coffee *Arabica* Fruit Extract | Present |
| E | Not present | Present | See column "Additional Antioxidants" | Tetrahexyldecyl Ascorbate, Tocopheryl Acetate, Tocotrienols, Ergothioneine, Ubiquinone, *Rubus Fruticosus* (Blackberry) Leaf Extract, *Saccharomyces* Ferment Lysate Filtrate, *Camellia Oleifera* Leaf Extract |

Product A was freshly prepared by Neocutis Inc., and Products B, C, D and E were tested after purchase from different internet retailers. Two to three manufacturing lots were tested for each product. Products B, C, D and E did not bear any expiration dates and were tested within about one month after purchase. They were unopened until the day of testing.

In order to evaluate the antioxidant stability, Product A was placed in a temperature control chamber at 40° C. and antioxidative capacity measurements were performed after 1, 4, 8 and 12 weeks.

Results:

The antioxidant power (AP) and reaction time of the five different test products are shown in FIGS. 1A and 1B, respectively. While three different lots were evaluated for Products A, B, C and E, only two different lots were evaluated for Product D. Of the test products, Product A provided the highest AP with the fastest reaction time $t_r$. Products A, B and C provided high antioxidant capacities, and Products D and E demonstrated low antioxidant capacities as determined by the selected ESR methodology under the present conditions.

Product A was demonstrated to remain relatively stable when kept at 40° C. over 12 weeks, which is representative of about two years shelf-life at ambient temperatures since it lost only about 20% of its initial antioxidant power (FIG. 2). After 12 weeks at 40° C., Product A showed still a higher antioxidant power than all other test products at their baseline measure as determined by the selected ESR methodology under the present conditions.

Thus, Composition A surprisingly and unexpectedly provided a very high AP and a low reaction time. As shown above, the results for this composition are significantly superior compared to the other antioxidant compositions having a high levels of stabilized Vitamin C combined with other antioxidant or being composed of antioxidant combinations without Vitamin C.

Example 4

Antioxidant Capacity Ex Vivo without UV-Radiation for an Antioxidant Serum with 15% Micronized Ascorbic Acid and Combination of Additional Antioxidants Introduction:

The natural presence of enzymatic and non-enzymatic antioxidants provides skin with an effective antioxidative protection system. Skin's antioxidative potential can be measured by ESR spectroscopy after labeling skin with a semi-stable test radical as described in SÖFW Journal 132, 9, 2006. The test radical will be reduced by the antioxidant systems inside the epidermis and dermis over time. Skin's intrinsic antioxidative capacity can be enhanced by supplementation of skin with topical antioxidants, and this increase can be quantified in skin biopsies using ESR spectroscopy.

Materials and Methods:

The measurements were performed with the X-band ESR spectrometer Miniscope MS 300 (Magnettech, Germany) at the following settings: 50 G sweep width, 200 Gain, 1 G modulation amplitude, 20 mW attenuation, 3358 G central field, and 0.14 sec time constant. The test radical 2,2,6,6-tetramethyl piperidine-N-oxyl (TEMPO; another example of a nitroxide probe) was obtained from Sigma-Aldrich, Munich, Germany. Pig ears obtained from the local slaughterhouse were washed, the subdermal fat was removed, and the skin was then cut in about 2 cm×2 cm pieces. Only freshly obtained, non-frozen skin was used. After application of the test products onto the skin surface at about 2 mg per cm², the skin pieces were placed for five minutes onto a filter paper saturated with an aqueous solution of 1 mM TEMPO. Afterwards, a skin biopsy of 4 mm was taken and placed in a custom manufactured ESR tissue holder and the ESR spectrum of the test radical was recorded after 5, 10 and 30 minutes. The kinetic parameter k was obtained from the function of the amplitude of the ESR spectra over measurement time using a mono-exponential first order decay function. The kinetic parameter k was determined for the test product and compared to the kinetic parameter k of the vehicle treated skin. All values were normalized to the vehicle treated skin. One lot of each Product A and Product B were evaluated in this test (Table 3). A freshly prepared ethanol/water solution of 1% α-tocopherol served as positive control. Four biopsies per test product and time point were measured. Only Product A is a composition according to the present invention.

Results:

Product A and Product B both significantly increased skin's antioxidant capacity as compared to their vehicles (FIG. 3). This increase was noticeable already after a short application time of the test product, what indicates that the antioxidants in both test products penetrate skin well and are active. After 5 to 10 minutes of application of Product A, the antioxidant capacity of skin was about doubled due to the antioxidants supplemented through Product A. After 30 minutes, the antioxidant capacity of skin was about 3-times higher than without antioxidant supplementation. As determined by the selected ESR methodology under the present conditions, Product A provided a more pronounced antioxidant protection with prolonged application time as compared to Product B. The 1% α-tocopherol solution only slightly enhanced the antioxidant capacity of skin and only for a short period of time. In contrast to Product A, α-tocopherol was unable to ensure a prolonged antioxidant protection possibly due to oxidation in skin.

Furthermore, Product A did only increase the antioxidant capacity of skin after topical application what demonstrates that Product A does not lead to pro-oxidative effects after topical application onto skin (i.e., decreases the antioxidant capacity of skin).

Example 5

Antioxidant Capacity Ex Vivo with UV Radiation for an Antioxidant Serum with 15% Micronized Ascorbic Acid and Combination of Additional Antioxidants Introduction:

Sun exposure leads to free radical formation in skin. At the same time, the antioxidant system of skin neutralizes the free radical formed by solar UV radiation, while the skin's natural antioxidant capacity is reduced as a result of this oxidative stress. ESR spectroscopy is also well suited to quantify the influence of UV radiation on skin's antioxidative capacity, with and without the presence of topical antioxidants.

Materials and Methods:

The ESR-measurements were performed as described without UV radiation and the same lots of each Product A and Product B were evaluated (Table 3). In this test, the skin was additionally exposed to solar simulated UV radiation using the Oriel 300 W Solar Simulator (Newport, Stratford, Conn.) at UV irradiances of $E_{280-320\ nm}=23.5$ $Wm^{-2}$ and $E_{320-400\ nm}=180$ $Wm^{-2}$.

The test product was applied for 30 min at about 2 mg per $cm^2$ onto freshly prepared pig skin ex vivo, which corresponded to the time period found to provide the highest antioxidant capacity in Example 4, supra. The skin was then exposed to solar simulated UV radiation of about 2.7 J $cm^{-2}$ and corresponding to 0.45 MED, which lead to a decrease in skin's intrinsic (i.e., vehicle treated skin without UV) antioxidant capacity by about 50%. Four biopsies per test product and time point were measured.

The kinetic parameter k was obtained from the function of the amplitude of the ESR spectra over measurement time using a mono-exponential first order decay function. The kinetic parameter k was determined for the vehicle and UV-treated skin, and the respective test product. All values were normalized to the vehicle treated but non-UV irradiated skin.

Results:

Product A and Product B both significantly increased skin's antioxidant capacity as compared to their vehicles also under conditions of solar UV exposure. Product A increased skin's antioxidant capacity by 205±13% after 30 min topical application. While Product B increased skin's antioxidant capacity by only 139±9%, a 1% α-tocopherol solution did not result in any increase (0%).

Furthermore, Product A did only increase the antioxidant capacity of skin after topical application what demonstrates that Product A does not lead to pro-oxidative effects after topical application onto skin also in combination with solar UVR exposure (i.e., decreases the antioxidant capacity of skin).

Example 6

UV-induced Skin Damage in Full-Thickness Skin Model

Introduction:

The use of full-thickness skin models allows evaluation of the efficacy of antioxidants after topical application and, therefore, represents a valuable in vitro method for trying to predict effects in humans. Sun exposure leads to free radical formation what ultimately causes skin damage including sun burn formation, DNA damage and protein oxidation.

Materials and Methods:

Full-thickness human skin model EpiDerm-FT™ (EFT-400) was obtained from MatTek Corporation (Ashland, Mass.). Skin tissues were exposed topically to 10 µl test product per $cm^2$ for 24 h prior to irradiation with 200 mJ $cm^{-2}$ simulated solar UV (Honle-500 solar lamp; Honle UV America, Marlboro, Mass.) or sham irradiation (controls). During the UV irradiation period, the tissues were transferred to culture plates containing 2 ml of phosphate buffered saline (basolateral compartment), then returned to fresh culture medium, and re-dosed with 10 µl $cm^{-2}$ of the respective test product for an additional 24 h. At the conclusion of the 24 h post-irradiation period, three tissues per condition were collected for histology and p53 immunostaining. Following treatment, tissues were fixed in 10% neutral-buffered formalin overnight and transferred to PBS the next day. Tissues were then bisected (to provide a cross-section), dehydrated in a series of graded ethanol, and embedded in paraffin. Five micron sections were prepared and stained with hematoxylin & eosin (H&E) or left unstained for immunohistochemistry.

Prior to immunostaining, the slides were de-paraffinized and rehydrated in PBS. Antigen retrieval was performed by heating the slides in 0.05% citraconic anhydride to 98° C. for 45 minutes. After cooling, the samples were blocked for 1 hour at room temperature with 10% normal goat serum/1% BSA in PBS. Primary antibody (anti-p53, clone DO7; obtained from Dako Denmark) was diluted in 1% BSA/PBS and incubated at room temperature for 1 hour at the a 1:25 dilution. Following incubation with primary antibody, slides were washed two times in 5×TBS and one time in 1×TBS. Secondary antibody (goat anti-mouse 488, AlexaFluor; obtained from Molecular Probes) was diluted 1:400 in 1% BSA/PBS and incubated with the samples for 1 hour at room temperature. Following incubation with secondary antibody, slides were rinsed two times in 1×TBS and stained with DAPI (0.1 µg/mL). Samples were washed 1× in TBS and mounted in Immu-Mount™ (Thermo Scientific). Following immunostaining, ten random fields were captured using a 20× objective. p53-Positive cells contained within epidermal cells were scored and counted. Only Product A is a composition according to the present invention.

Results:

UV irradiation of untreated skin led to formation of sunburn cells (cells with pyknotic nuclei and eosinophilic cytoplasm) the basal layers of the tissues (FIG. 4). Minor vacuolization within the epidermis was also evident from the histological analysis after H&E staining. No sunburn cells and a normal histology except some minor vacuolization in one out of three tissues were observed when skin was pre-treated with Product A (FIG. 4). This observation indicates that Product A helps protect skin from oxidative stress induced damages.

Figure 5:
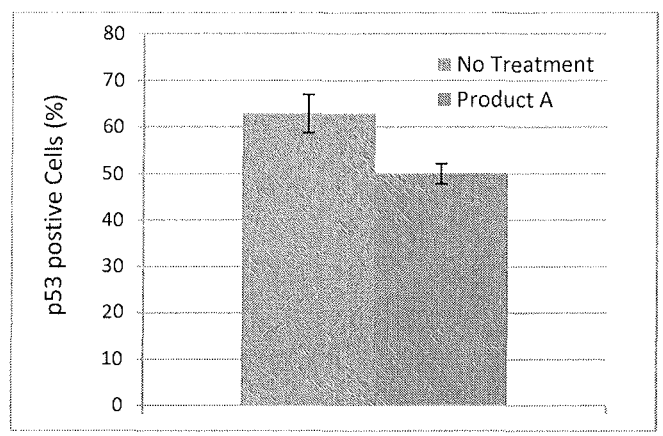
FIG. 5 shows p53 expression in a full-thickness human skin model 24 h after irradiation with solar simulated UVB-light as a function of treatment with Product A. The percentage of p53 positive keratinocytes are shown (mean±standard deviation, n=3).

Product A significantly protected epidermal cells from p53 induction as compared to non-treated skin after ITV-exposure (FIG. 5). Product A reduced the percentage of p53 positive cells by about 13%. p53 is a the tumor suppressor protein acting as transcription factor and plays an essential role in the cellular response to UV or chemically induced genotoxic stress. By blocking the cell cycle in cells which have suffered an excessive DNA damage, p53 prevents replication of damaged DNA as long as it has not been repaired. In case of unsuccessful reparation, p53 induces apoptosis. The reduced p53 expression observed with Product A can be associated with the occurrence of less DNA damage as a result of topical supplementation of skin with antioxidants. p53 is also essential in the formation of sunburn cells.

Example 7

UV-induced Skin Damage in Humans

Introduction:

The objective of this study was to determine the potential of an antioxidant product to reduce UV-induced erythema when applied over four days before solar simulated UV-irradiation and once two hours post-irradiation in humans.

Materials and Methods:

Eleven female subjects of Fitzpatrick skin photo-type II or III, ranging in age from 25 to 65 years, were enrolled. The lower back, lateral to the mid-line, was selected as test area, as it was free of sunburn, scars, active dermatitis, uneven skin tones, and/or excessive hair. Subjects were instructed to minimize their exposure to sunlight and to abstain from all sunbathing, swimming, and tanning bed usage for the course of the trial. A single port xenon arc solar simulator (300 W) was used as the source of full spectrum UV radiation (Solar Light Company, Philadelphia, Pa.). This instrument provided a spectral output in the ultraviolet range comparable to that of natural sunlight. The WG320 and UG11 filters were used to provide a full spectrum of UV, with wavelength ranges of 290-400 nm. The solar simulator was provided an appropriate warm-up period, after which, it was expected to have no significant time-related fluctuations in radiation emissions. The solar simulator had good beam uniformity in the exposure plane. To ensure that the solar simulator delivers the appropriate spectrum of UV radiation, its spectral output is measured quarterly with an accurately calibrated spectro-radiometer. The lamp output was measured after warm-up with a UV intensity meter (Model PMA2100, Solar Light Company, Philadelphia, Pa.) equipped with the appropriate detector before and after the test period.

The Minimal Erythemal Dose (MED) of each subject was determined by a progressive sequence of timed UV light exposures, each of which was graduated incrementally by 25% over that of the previous exposure. The MED was defined as the time interval or dosage of UV light irradiation sufficient to produce a minimal, perceptible erythema on untreated skin. Approximately 24 hours after irradiation, the MED test sites were evaluated for erythema according to the following erythema scoring scale:

0 no reaction
0.5 equivocal reaction, barely perceptible erythema with no clearly defined border
1 mild but definite erythema with clearly defined borders
2 moderate clearly defined erythema
3 strong erythema, edema
4 bulla or vesiculation The subjects had two test sites of 11 cm×5 cm demarcated on their back. One site received approximately 2 mg cm$^{-2}$ Product A (Table 3) once per day for four consecutive days whereas the other site was left untreated and served as UV-irradiated control. The test sites were randomized.

Approximately 30-minutes after the last application, the treated test site and the control site were divided into 5 sub-sites and irradiated with 1, 1.5, 2, 2.5, or 3-times the subject's predetermined MED, respectively. Two hours after completion of the irradiation, Product A was re-applied at approximately 2 mg cm$^{-2}$ to the appropriate test site while the control site was left untreated.

Approximately 24 hours after irradiation, the test sites were evaluated visually using the erythema scoring scale as described above. In addition, digital photographs using a Nikon D-90 digital SLR with 60 mm lens under fixed lighting were taken. In order to measure the erythema levels, skin color readings were conducted instrumentally with the Smart Probe 400 Colorimeter (IMS Testing Group, Milford, Conn.). The a*-value of the L*a*b* color notation system is indicative of color changes in the red-green color axis. The greater the value of a*, the more intensely red the object being evaluated. Therefore, the a*-value was used as a measure of redness (erythema) on the skin surface, where an increase indicates an increase in erythema. Colorimeter measurements were made in triplicate and the average was used as the data point.

Results:

All 11 subjects (45±12 years of age) qualified and completed the trial. No adverse events including any erythema score of three or greater were observed. Their MED ranged between 12.7 and 48.1 mJ cm$^{-2}$; with an average of 24.1±11.1 mJ cm$^{-2}$.

Figure 6:
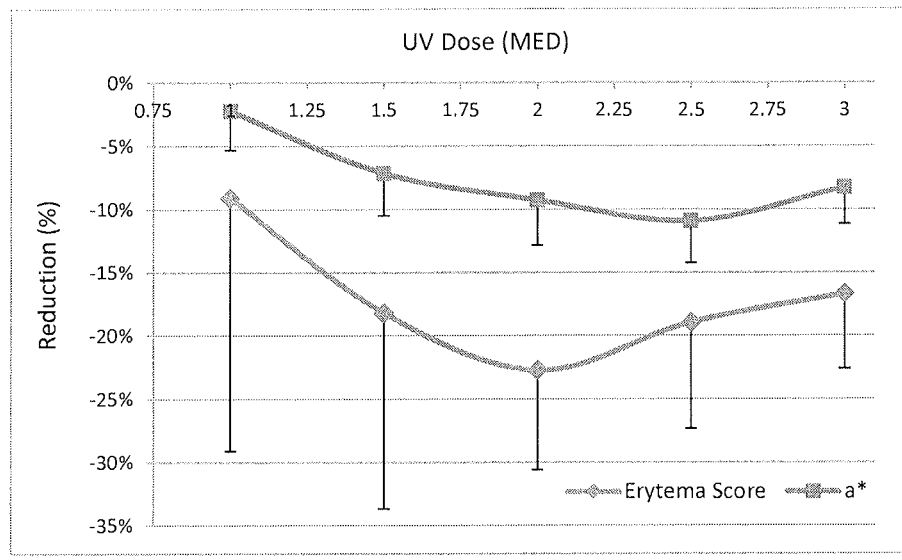
FIG. 6 shows reduction of erythema response 24 h after irradiation with between 1 to 3 MED in humans as assessed visually (erythema score) and by colorimetry (a*) when skin was treated with Product A (mean with negative standard deviation are shown; n=11).

As determined by visual assessment 24 h after irradiation with between 1 to 3 MED, an up to 23% (average of 11 subjects) reduction of solar UV induced skin erythema was observed with Product A as compared to the non-treated skin site (FIG. 6). Likewise, as determined by colorimeter 24 h after irradiation with between 1 to 3 MED, an up to 11% (average of 11 subjects) reduction in the a*-value was measured with Product A as compared to the non-treated skin site (FIG. 6).

Figure 7:
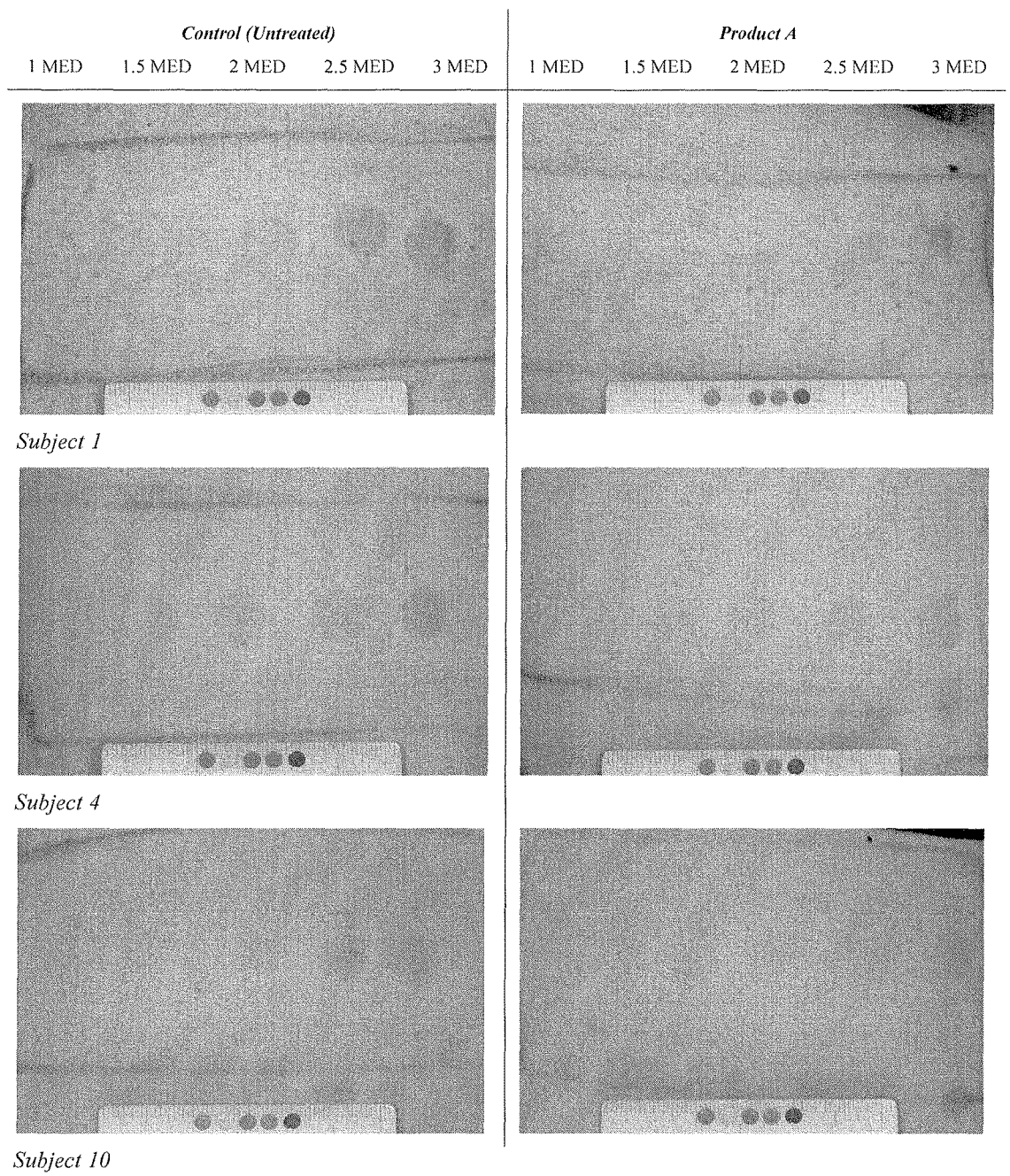
FIG. 7 shows examples of clinical photographs of the Product A treated and the non-treated (control) study sites on the lower back 24 h after solar simulated UV-irradiation corresponding to 1, 1.5, 2, 2.5, and 3 MED for three different subjects.

The photographs of the treated and non-treated study sites on the lower back for few of the subjects are shown FIG. 7. The photographs were taken under fixed lighting.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

We claim:

1. An antioxidant composition comprising at least one topically acceptable silicone oil in combination with an effective amount of Vitamin C, Vitamin E, and one or more polyphenol antioxidants.

2. The antioxidant composition of claim 1, wherein the composition further comprises at least one additional antioxidant.

3. The antioxidant composition of claim 2, wherein the at least one additional antioxidant is creatine.

4. The antioxidant composition of claim 1, wherein the composition further comprises at least one low molecular weight chromane or chromene derivative with antioxidant properties.

5. The antioxidant composition of claim 3, wherein the composition further comprises at least one low molecular weight chromane or chromene derivative with antioxidant properties.

6. The antioxidant composition of claim 1, wherein Vitamin C is present in an amount between 1 and 30%.

7. The antioxidant composition of claim 1, wherein Vitamin E is present in an amount between 0.1 and 5%.

8. The antioxidant composition of claim 3, wherein creatine is present in an amount between 0.1 and 5%.

9. The antioxidant composition of claim 4, wherein the at least one low molecular weight chromane or chromene derivative with antioxidant properties is dimethylmethoxy chromanol.

10. The antioxidant composition of claim 5, wherein the at least one low molecular weight chromane or chromene derivative with antioxidant properties is dimethylmethoxy chromanol.

11. The antioxidant composition of claim 9, wherein the dimethylmethoxy chromanol is present in an amount between 0.01 and 1%.

12. The antioxidant composition of claim 10, wherein the dimethylmethoxy chromanol is present in an amount between 0.01 and 1%.

13. The antioxidant composition of claim 1, wherein the silicone oil is cyclopentasiloxane or a combination of cyclopentasiloxane and polysilicone-11.

14. The antioxidant composition of claim 1, wherein the one or more polyphenol antioxidants is selected from the group consisting of flavonoids; flavonols; flavones; catechins; flavanones; anthocyanidins; isoflavonoids; extracts from green tree extracts, milk thistle, soybeans, wine grapes and their seeds, acai berry, coffee berry, feverfew, pomegranate, tropical ferns, and turmeric; and any combinations thereof.

15. The antioxidant composition of claim 14, wherein the polyphenol antioxidant is epigallocatechin gallate (EGCG).

16. The antioxidant composition of claim 15, wherein the epigallocatechin gallate (EGCG) is present in an amount between 0.01 and 0.5%.

17. The antioxidant composition of claim 1, wherein Vitamin C is present in an amount between 1 and 30%, Vitamin E is present in an amount between 0.1 and 5%, and the one or more polyphenol antioxidants is epigallocatechin gallate (EGCG) present in an amount between 0.01 and 0.5%.

18. The antioxidant composition of claim 17, wherein the composition further comprises a low molecular weight chromane or chromene derivative with antioxidant properties, wherein the low molecular weight chromane or chromene derivative with antioxidant properties is dimethylmethoxy chromanol present in an amount between 0.01 and 0.5%.

19. The antioxidant composition of claim 18, wherein the composition further comprises creatine present in an amount between 0.1 and 5%.

20. The antioxidant composition of claim 17, wherein the composition further comprises creatine present in an amount between 0.1 and 5%.

21. The antioxidant composition of claim 1, wherein the composition further comprises one or more carriers or excipients suitable for topical administration or subcutaneous administration.

22. The antioxidant composition of claim 1, wherein the Vitamin C is micronized Vitamin C.

23. The antioxidant composition of claim 1, wherein the composition is substantially free of water.

24. The composition of claim 1, wherein the composition further comprises one or more additional active ingredients.

25. A pharmaceutical composition comprising the composition of claim 1 and one or more pharmaceutically acceptable carriers.

26. A cosmetic composition comprising the composition of claim 1 and one or more cosmetically acceptable carriers.

27. A kit comprising, in one or more containers, the pharmaceutical composition of claim 25 and instructions for use.

28. A kit comprising, in one or more containers, the cosmetic composition of claim 26 and instructions for use.

29. A method of treating, alleviating, or ameliorating a symptom, condition, disorder, or disease associated with free radicals, the method comprising administering an effective amount of the composition of claim 1 to a patient in need thereof.

30. The method of claim 29, wherein the symptom, condition, disorder, or disease associated with free radicals is selected from the group consisting of sun induced skin damages, skin aging, skin inflammatory diseases or disorders, skin degenerative diseases or disorders, and cancer.

31. The method of claim 29, wherein treating, alleviating, or ameliorating the symptom neutralizes free radicals.

32. The method of claim 29, wherein the method comprises the repeated topical administration of the composition to the patient.

33. The method of claim 32, wherein the composition is administered to the patient at least once or twice a day for at least 30 days.

34. The method of claim 29, wherein the method comprises the repeated subcutaneous administration of the composition to the patient.

35. The method of claim 34, wherein the composition is administered to the patient at least once or twice a day for at least 30 days.

36. A method for modifying free radical damage to skin by administering an effective amount of the composition of claim 1 to the skin of a patient.

37. The method of claim 36, wherein the effective amount is sufficient to treat, prevent, or treat and prevent free radical damage to the skin.

* * * * *

UNITED STATES PATENT AND TRADEMARK OFFICE
CERTIFICATE OF CORRECTION

PATENT NO.         : 9,713,604 B2                                                        Page 1 of 1
APPLICATION NO.    : 14/258074
DATED              : July 25, 2017
INVENTOR(S)        : Frank Dreher It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this

Twenty-fifth Day of September, 2018

Andrei Iancu
*Director of the United States Patent and Trademark Office*